US007556751B2

United States Patent
Chopra et al.

(10) Patent No.: US 7,556,751 B2
(45) Date of Patent: *Jul. 7, 2009

(54) PHOTOCHROMIC MATERIALS HAVING ELECTRON-WITHDRAWING SUBSTITUENTS

(75) Inventors: Anu Chopra, Pittsburgh, PA (US); Beon-Kyu Kim, Gibsonia, PA (US); Barry Van Gemert, Pitcairn, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 385 days.

This patent is subject to a terminal disclaimer.

(21) Appl. No.: 11/314,141

(22) Filed: Dec. 21, 2005

(65) Prior Publication Data

US 2007/0138449 A1     Jun. 21, 2007

(51) Int. Cl.
G02B 5/23 (2006.01)

(52) U.S. Cl. .................... 252/586; 549/352; 549/382; 544/149

(58) Field of Classification Search ......... 252/582–589; 428/412, 424.2, 441–442, 461–463, 500–523
See application file for complete search history.

(56) References Cited

U.S. PATENT DOCUMENTS

| 5,458,814 | A |   | 10/1995 | Kumar et al. | 252/586 |
| 5,645,767 | A |   | 7/1997  | Van Gemert | 252/586 |
| 5,955,520 | A | * | 9/1999  | Heller et al. | 524/87 |
| 6,025,026 | A |   | 2/2000  | Smith et al. | 427/316 |
| 6,068,797 | A |   | 5/2000  | Hunt | 264/1.7 |
| 6,113,814 | A |   | 9/2000  | Gemert et al. | 252/586 |
| 6,146,554 | A | * | 11/2000 | Melzig et al. | 252/586 |
| 6,150,430 | A |   | 11/2000 | Walters et al. | 522/79 |
| 6,296,785 | B1 | * | 10/2001 | Nelson et al. | 252/586 |
| 6,555,028 | B2 |   | 4/2003  | Walters et al. | |
| 2001/0025948 | A1 |   | 10/2001 | Walters et al. | |
| 2003/0071247 | A1 |   | 4/2003  | Petrovskaia et al. | |
| 2003/0165686 | A1 |   | 9/2003  | Blackburn et al. | 428/412 |
| 2004/0185268 | A1 |   | 9/2004  | Kumar et al. | |
| 2004/0186241 | A1 |   | 9/2004  | Gemert | |
| 2004/0191520 | A1 |   | 9/2004  | Kumar et al. | |
| 2005/0012998 | A1 |   | 1/2005  | Kumar et al. | |
| 2005/0151926 | A1 |   | 7/2005  | Kumar et al. | 351/163 |
| 2005/0258408 | A1 |   | 11/2005 | Molock et al. | |
| 2006/0022176 | A1 |   | 2/2006  | Wang et al. | |
| 2006/0226400 | A1 | * | 10/2006 | Xiao et al. | 252/582 |
| 2006/0226401 | A1 | * | 10/2006 | Xiao et al. | 252/586 |
| 2006/0226402 | A1 | * | 10/2006 | Kim et al. | 252/586 |
| 2006/0227287 | A1 |   | 10/2006 | Molock et al. | |
| 2006/0228557 | A1 | * | 10/2006 | Kim et al. | 428/411.1 |
| 2007/0138448 | A1 | * | 6/2007  | Chopra | 252/582 |

FOREIGN PATENT DOCUMENTS

| DE | 295 22 188 U 1 | 8/2000 |
| JP | 2004-131593 | 4/2004 |
| WO | WO 96/14596 | 5/1996 |
| WO | WO 01/19813 | 3/2001 |
| WO | WO 01/36406 A1 | 5/2001 |
| WO | WO 01/70719 A2 | 9/2001 |
| WO | WO 02/053553 | 7/2002 |
| WO | WO 2005/005570 A1 | 1/2005 |
| WO | WO 2006/110306 A1 | 10/2006 |

OTHER PUBLICATIONS

Lang's Handbook of Chemistry, McGraw Hill, 15th Edition, 1999, pp. 9.1-9.8, J. A. Dean, "Section 9 Physiocochemical Relationships".

* cited by examiner

*Primary Examiner*—Ling-Siu Choi
*Assistant Examiner*—Bijan Ahvazi
(74) *Attorney, Agent, or Firm*—Linda Pingitore; Frank P. Mallak; Deborah M. Altman

(57) ABSTRACT

Photochromic materials comprising indeno-fused naphthopyrans having a first electron-withdrawing substituent and, in certain non-limiting embodiments, a second electron-withdrawing substituent are disclosed. The photochromic materials according to the various embodiments may display faster fade rates, bathochromic shift, and higher performance ratings compared to comparable indeno-fused naphthopyrans without the electron-withdrawing substituents. Photochromic compositions and articles, such as optical elements, incorporating the photochromic materials are also disclosed.

25 Claims, 7 Drawing Sheets

PHOTOCHROMIC MATERIALS HAVING ELECTRON-WITHDRAWING SUBSTITUENTS

BACKGROUND

Various non-limiting embodiments of the present disclosure relate to photochromic materials comprising indeno-fused naphthopyrans with substituents comprising one or more electron-withdrawing groups. According to certain non-limiting embodiments, the indeno-fused naphthopyrans may also comprise substituents comprising electron-donating groups and/or electron-withdrawing groups located at the para position of a phenyl ring bonded to the 3-position of the indeno-fused naphthopyran. The photochromic materials according to various non-limiting embodiments of the present disclosure may also exhibit faster fade rates as compared to similar indeno-fused naphthopyrans without the electron-withdrawing substituents. Other non-limiting embodiments disclosed herein relate to photochromic compositions and articles, such as optical elements, incorporating the same.

Many conventional photochromic materials, such as, for example, photochromic naphthopyrans, can undergo a transformation from a first form or state to a second form or state in response to the absorption of electromagnetic radiation. For example, many conventional thermally reversible photochromic materials are capable of transforming between a first "clear" or "bleached" ground-state form and a second "colored" activated-state form in response to the absorption of certain wavelengths of electromagnetic radiation (or "actinic radiation"). As used herein with reference to photochromic materials, articles and compositions, the terms "clear" and "bleached" mean the photochromic material, article, or composition is substantially without color, that is, has substantially no absorption of electromagnetic radiation within the visible region of the electromagnetic spectrum (420 nm-700 nm). As used herein the term "actinic radiation" refers to electromagnetic radiation that is capable of causing a photochromic material to transform from a first form or state to a second form or state. The photochromic material may then revert back to the clear ground-state form in response to thermal energy in the absence of actinic radiation. Photochromic articles and compositions that contain one or more photochromic materials, for example, photochromic lenses for eyewear applications, generally display optically clear and colored states that correspond to the photochromic material(s) that they contain. Thus, for example, eyewear lenses that contain photochromic materials can transform from a clear state to a colored state upon exposure to actinic radiation, such as certain wavelengths found in sunlight, and can revert back to the clear state in the absence of such radiation upon absorption of thermal energy.

When utilized in photochromic articles and compositions, conventional photochromic materials are typically incorporated into a host polymer matrix by one of imbibing, blending, and/or bonding. Alternatively, the photochromic material may be imbibed into a pre-formed article or coating. As used herein, the term "photochromic composition" refers to a photochromic material in combination with one or more other material, which may or may not be a different photochromic material.

For many photochromic applications, it is generally desirable to have a photochromic material that can rapidly revert from the colored, activated-state form to the clear, ground-state form, while still maintaining acceptable characteristics such as color density. For example, in photochromic eyewear applications, optical lenses comprising photochromic materials transform from an optically clear state to a colored state as the wearer moves from a region of low actinic radiation, such as indoors, to a region of high actinic radiation, such as into direct sunlight. As the lenses become colored, less electromagnetic radiation from the visible and/or ultraviolet regions of the electromagnetic spectrum is transmitted through the lens to the wearer's eyes. In other words, more electromagnetic radiation is absorbed by the lens in the colored state than in the optically clear state. When the wearer subsequently moves from the region of high actinic radiation back to a region of low actinic radiation, the photochromic material in the eyewear reverts from the colored, activated-state form to the clear, ground-state form in response to thermal energy. If this transformation from colored to clear takes several minutes or more, the wearer's vision may be less than optimal during this time due to the combined effect of the lower ambient light and the reduced transmission of visible light through the colored lenses.

Accordingly, for certain applications, it may be advantageous to develop photochromic materials that can more quickly transition from the colored form to the clear form, as compared to conventional photochromic materials. As used herein, the term "fade rate" is a measurement of the rate at which the photochromic material transforms from the activated colored state to the unactivated clear state. The fade rate for a photochromic material may be measured, for example, by activating a photochromic material to saturation under controlled conditions in a given matrix, measuring its activated steady state absorbance (i.e., saturated optical density) and then determining the length of time it takes for the absorbance of the photochromic material to decrease to one-half the activated steady state absorbance value. As measured in this fashion, the fade rate is designated by $T_{1/2}$, with units of seconds.

Additionally, as mentioned above, typically the transformation between the ground-state form and the activated-state form requires that the photochromic material be exposed to certain wavelengths of actinic radiation. For many conventional photochromic materials, the wavelengths of actinic radiation that may cause this transformation typically range from 320 nanometers ("nm") to 390 nm. Accordingly, conventional photochromic materials may not be optimal for use in applications that are shielded from a substantial amount of actinic radiation in the range of 320 nm to 390 nm. Therefore, for some applications, it may be advantageous to develop photochromic materials that can have a ground-state form absorption spectrum for electromagnetic radiation that is bathochromically shifted. As used herein, the term "bathochromically shifted" means having an absorption spectrum for electromagnetic radiation that is shifted to longer wavelength values. Thus a photochromic material that has a bathochromically shifted ground-state form absorption spectrum will require absorption of actinic radiation having a longer wavelength in order to transition from the ground-state form to the activated-state form.

For example, lenses for eyewear applications that are made using conventional photochromic materials may not reach their fully-colored activated-state form when used in an automobile. This is because a large portion of electromagnetic radiation in the range of 320 nm to 390 nm can be absorbed by the windshield of the automobile before it can be absorbed by the photochromic material(s) in the lenses. In certain applications, such as those involving behind the windshield use of photochromic materials, it may be advantageous if the ground-state form absorption spectrum of the photochromic material were bathochromically shifted such that the photochromic material may absorb sufficient electromagnetic radiation having a wavelength greater than 390 nm to permit the photochromic material to transform from the ground-state form to the activated-state form.

The absorption spectrum of a photochromic material in the activated-state form will correspond to the color of the medium or article containing the photochromic material, for example, the color of the eyewear lens, when exposed to actinic radiation. As specific wavelengths within the visible region of electromagnetic radiation are absorbed by a photochromic material in the activated-state form, the wavelengths within the visible region that are transmitted (i.e., not absorbed) correspond to the color of the photochromic material in the activated-state form. For example, absorption of wavelengths of light around about 500 nm to about 520 nm in the visible region of the electromagnetic spectrum results in a photochromic material that exhibits a "reddish" color, i.e., it absorbs visible radiation from the short wavelength or blue end of the visible spectrum and transmits radiation from the longer wavelength or red end of the visible spectrum. Conversely, absorption of wavelengths of light around about 580 nm to about 610 nm in the visible region of the electromagnetic spectrum results in a photochromic material that exhibits a "bluer" color, i.e., it absorbs visible radiation from the longer wavelength or red end of the visible spectrum and transmits radiation from the shorter wavelength or blue end of the visible spectrum.

Many current photochromic compounds have activated-state absorption spectrums that absorb visible light toward the blue end of the visible spectrum and exhibit a reddish color in the activated form. If the photochromic material has an activated-state absorption spectrum that is bathochromically shifted, i.e., shifted to absorb light having a longer wavelength, the photochromic material will exhibit a bluer color than the current photochromic material. For certain applications it may be desirable to have a photochromic material that has a bathochromically shifted activated form absorption spectrum for actinic radiation and which may therefore exhibit a bluer color.

BRIEF SUMMARY

Various non-limiting embodiments disclosed herein relate to photochromic materials having one or more electron-withdrawing substituents. Photochromic materials according to certain non-limiting embodiments may have faster fade rates and/or an activated and unactivated absorption spectra that are bathochromically shifted.

In one non-limiting embodiment, the photochromic material may comprise an indeno-fused naphthopyran and a first electron-withdrawing group bonded to the 6-position of the indeno-fused naphthopyran, wherein the substitution at the 13-position of the indeno-fused naphthopyran does not comprise hydroxyl. In certain non-limiting embodiments, the photochromic material may further comprise a second electron-withdrawing group bonded to the 11-position of the indeno-fused naphthopyran. The first electron-withdrawing group and the second electron-withdrawing group may be the same or different.

According to other non-limiting embodiments, the photochromic material may comprise an indeno-fused naphthopyran; a first electron-withdrawing group bonded to a carbon on the C ring of the indeno-fused naphthopyran; and a second electron-withdrawing group bonded to the 11-position of the indeno-fused naphthopyran, wherein substitution at the 13-position of the indeno-fused naphthopyran does not comprise hydroxyl.

According to still other non-limiting embodiments, the photochromic material may comprise an indeno-fused naphthopyran; a first electron-withdrawing group bonded to the 6-position of the indeno-fused naphthopyran; a second electron-withdrawing group bonded to the 11-position of the indeno-fused naphthopyran; and geminal dialkyl substitution at the 13-position of the indeno-fused naphthopyran. The first electron-withdrawing group and the second electron-withdrawing group may be the same or different.

According to further non-limiting embodiments of the present disclosure, the photochromic material may comprise an indeno-fused naphthopyran; a first electron-withdrawing group bonded to the 6-position of the indeno-fused naphthopyran; and a second electron-withdrawing group bonded to the 11-position of the indeno-fused naphthopyran, provided that if the first electron-withdrawing group is a fluoro group, then the second electron-withdrawing group is not a fluoro group.

Still further non-limiting embodiments of the present disclosure relate to a photochromic material having the structure as set forth in FIG. III:

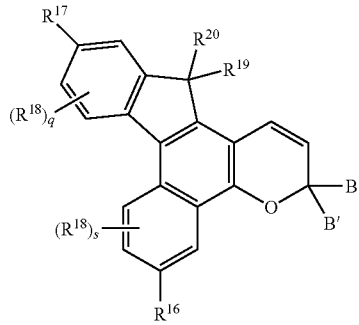

III wherein $R^{16}$, $R^{17}$, $R^{18}$, $R^{19}$, $R^{20}$, B and B' represent groups as described herein below and set forth in the claims.

Still other non-limiting embodiments relate to photochromic compositions, photochromic articles, such as optical elements, and methods of making the same, wherein the photochromic compositions and photochromic articles comprise a photochromic material according to various non-limiting embodiments disclosed herein.

BRIEF DESCRIPTION OF THE DRAWINGS

The various non-limiting embodiments disclosed herein may be better understood when read in conjunction with the following Figures.

DETAILED DESCRIPTION

Figure 1A:
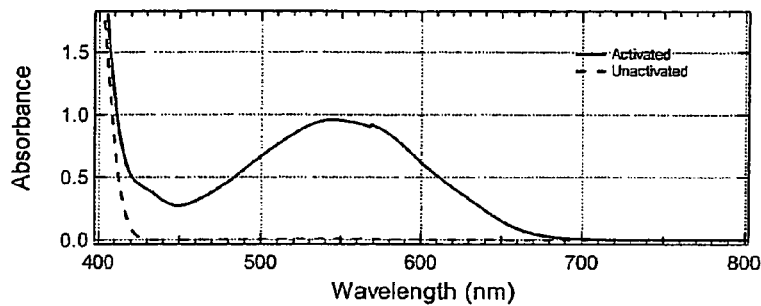
FIGS. 1A, 1B, 1C, 1D, 1E, and 1F illustrate the activated and unactivated absorption spectra within the visible region of the electromagnetic spectrum for various non-limiting embodiments of the photochromic materials of the present disclosure (spectra in FIGS. 1E and 1F are recorded at half concentration).
Figure 1A:
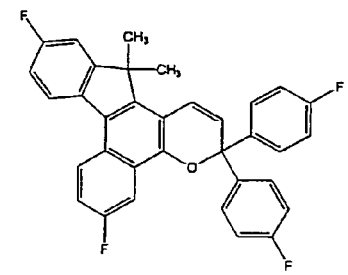
Figure 1B:
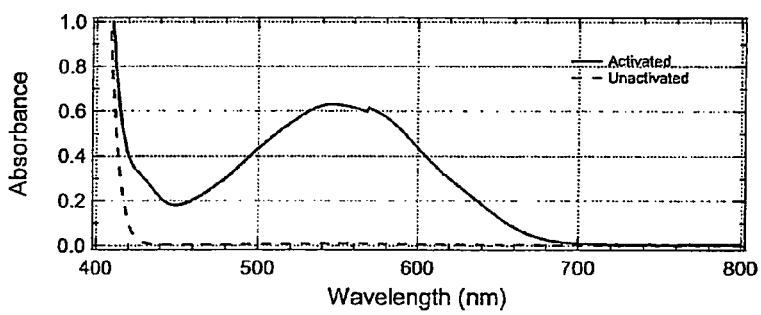
Figure 1B:
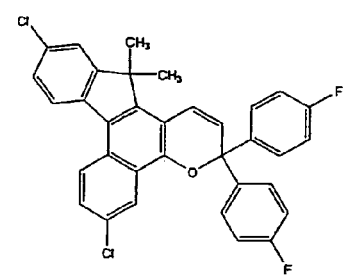
Figure 1C:
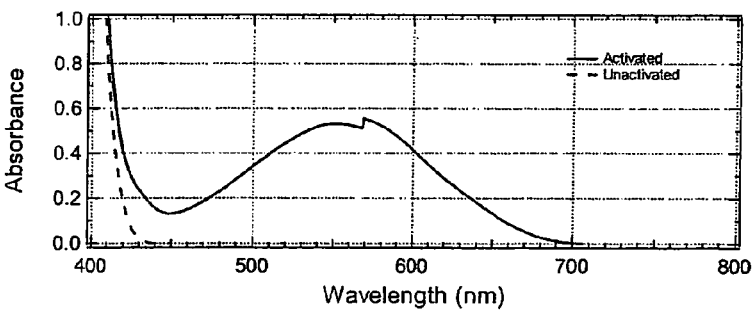
Figure 1C:
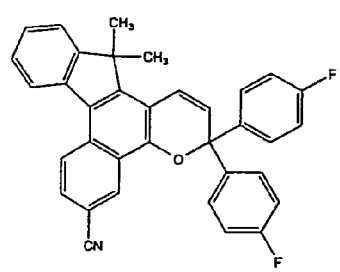
Figure 1D:
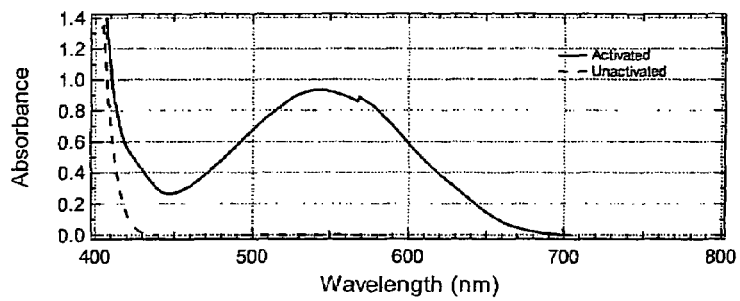
Figure 1D:
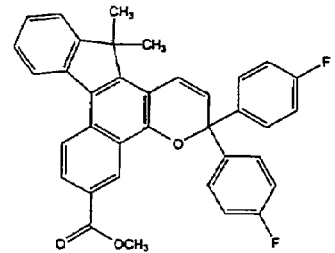
Figure 1E:
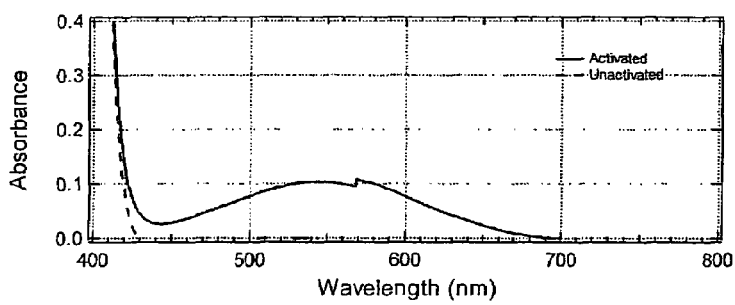
Figure 1E:
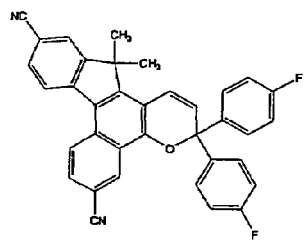
Figure 1F:
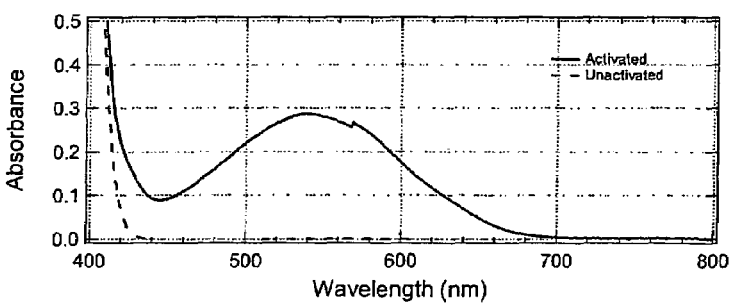
Figure 1F:
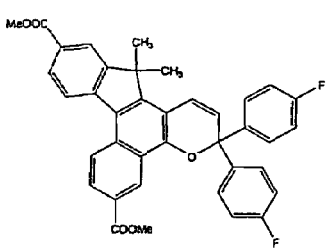

As used in this specification and the appended claims, the articles "a," "an," and "the" include plural referents unless expressly and unequivocally limited to one referent.

Additionally, for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

Photochromic compounds and materials according to the various non-limiting embodiments of the invention will now be discussed. As used herein, the term "photochromic" means having an absorption spectrum for at least visible radiation that varies in response to absorption of at least actinic radiation. As used herein the term "actinic radiation" refers to electromagnetic radiation that is capable of causing a photochromic material to transform from a first form or state to a second form or state. Further, as used herein, the term "photochromic material" means any substance that is adapted to display photochromic properties, i.e., adapted to have an absorption spectrum for at least visible radiation that varies in response to absorption of at least actinic radiation. As used herein, the term "photochromic composition" refers to a photochromic material in combination with one or more other material, which may or may not be a photochromic material.

As used herein, the term "indeno-fused naphthopyran" is defined as a photochromic compound having a ring skeleton comprising an indeno [2',3':3,4]naphtho[1,2-b]pyran, as shown below in (I). Indeno-fused naphthopyrans are examples of photochromic naphthopyrans. As used herein, the term "photochromic naphthopyrans" refers to naphthopyrans that are capable of transforming between a first "closed-form" and a second "open-form" in response to the absorption of actinic radiation. As used herein, the term "closed-form" corresponds to the unactivated, ground-state form of the indeno-fused naphthopyran and the term "open-form" corresponds to the activated-state form of the indeno-fused naphthopyran.

As used herein the terms "3-position," "6-position," "11-position," "13-position," and so forth refer to the 3-, 6-, 11-, and 13-position respectively of the ring atoms of the indeno-fused naphthopyran core, as illustrated by the numbered positions on (I) below. Further, the rings of the indeno-fused naphthopyran skeleton may be denoted by a letter from A to E, such that each ring may be referred to by its corresponding letter. Thus for example, as used herein, the terms "C ring" or "C ring of the indeno-fused naphthopyran" correspond to the lower ring of the naphthyl substructure of the indeno-fused naphthopyran, as denoted by the ring labeled "C" in structure (I) below. As used herein, the term "bonded to a carbon of the C ring" means bonded to a carbon in at least one of the 5-position, the 6-position, the 7-position, or the 8-position, according to the numbering set forth in structure (I).

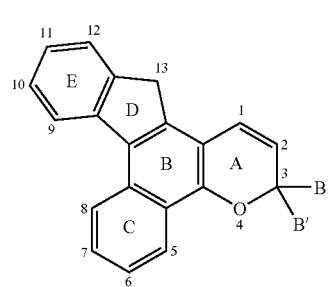

According to various non-limiting embodiments disclosed herein, the groups B and B' bonded to the carbon at the 3-position of the indeno-fused naphthopyran are part of the photochromic indeno-fused naphthopyran core illustrated above in (I). Without intending to be limited by any particular theory, it is believed that the B and B' groups may help stabilize the activated, open form of the indeno-fused naphthopyran structure by being in conjugation with the pi-system of the open-form of the indeno-fused naphthopyran structure. According to various non-limiting embodiments disclosed herein, the groups B and B' may be any structures that have at least one pi-bond capable of being in conjugation with the pi-system of the open-form of the core indeno-fused naphthopyran structure, for example, but not limited to, a substituted or unsubstituted aryl ring (e.g., a substituted or unsubstituted phenyl ring or naphthyl ring), substituted or unsubstituted heteroaromatic ring structures, or other structure as set forth herein below. As will be set forth in greater detail below, according to certain non-limiting embodiments wherein the B and/or B' groups comprise a substituted phenyl, the ortho, meta, and/or para position of the phenyl ring of the B and/or B' group may be substituted by a group, such as, for example, a fluoro group and/or an electron-donating group.

Various non-limiting embodiments of the present disclosure provide for a photochromic material comprising: an indeno-fused naphthopyran, and a first electron-withdrawing group bonded to the 6-position of the indeno-fused naphthopyran, wherein substitution at the 13-position of the indeno-fused naphthopyran does not comprise hydroxyl. The photochromic material according to certain non-limiting embodiments has a faster fade rate than a comparable photochromic material without a first electron-withdrawing group bonded to the 6-position of the indeno-fused naphthopyran. As used herein, the terms "group" or "groups" mean an arrangement of one or more atoms. As used herein, the term "electron-withdrawing group" may be defined as a group that withdraws electron density from a pi-system, such as, for example, the pi-system of the indeno-fused naphthopyran core structure. Further, an "electron-withdrawing group", as used herein, may be defined as a group having a positive Hammett $\sigma_p$ value, when the group is attached to a carbon participating in an aromatic pi-system, such as the aromatic pi-system of the indeno-fused naphthopyran core. As used herein, the term "Hammett $\sigma_p$ value" is a measurement of the electronic influence, as either an electron-donating or electron-withdrawing influence, of a substituent attached to a carbon participating in an aromatic pi system that is transmitted through the polarizable pi electron system, such as, for example, an aromatic pi electron system. The Hammett $\sigma_p$ value is a relative measurement comparing the electronic influence of the substituent in the para position of a phenyl ring to the electronic influence of a hydrogen substituted at the para position. Typically for aromatic substituents in general, a negative Hammett $\sigma_p$ value is indicative of a group or substituent having an electron-donating influence on a pi electron system (i.e., an electron-donating group) and a positive Hammett $\sigma_p$ value is indicative of a group or substituent having an electron-withdrawing influence on a pi electron system (i.e., an electron-withdrawing group).

As used herein, the term "electron-donating group" may be defined as a group that donates electron density into a pi-system, such as, for example, of the indeno-fused naphthopyran core structure. Examples of an "electron-donating group" may include an atom bonded directly to the pi-system of the photochromic material, wherein the atom has at least one lone pair of electrons which are capable of delocalization into the pi system of the aromatic ring structure, and/or the group may donate electron density into the pi system by an inductive effect, such as, for example, an alkyl substituent. Further, an "electron-donating group", as used herein, may be defined as a group having a negative Hammett $\sigma_p$ value, when the group is attached to a carbon participating in an aromatic pi system.

Electron-withdrawing groups suitable for use in connection with various non-limiting embodiments of the photochromic material described herein may have a Hammett $\sigma_p$ value ranging from about 0.05 to about 0.75. Suitable electron-withdrawing groups may comprise, for example and without limitation: halogen, such as fluoro ($\sigma_p$=0.06), chloro ($\sigma_p$=0.23), and bromo ($\sigma_p$=0.23); perfluoroalkyl (for example, —$CF_3$, $\sigma_p$=0.54) or perfluoroalkoxy (for example, —$OCF_3$, $\sigma_p$=0.35), where the perfluoroalkyl portion of either the perfluoroalkyl or the perfluoroalkoxy may comprise, for example, trifluoromethyl or other perfluoroalkyl portions having the formula $C_nF_{2n+1}$, where 'n' is an integer from 1 to 10; cyano ($\sigma_p$=0.66); —OC(=O)$R^0$ (for example, —OC(=O)$CH_3$, $\sigma_p$=0.31); —$SO_2$X (for example, —$SO_2CH_3$, $\sigma_p$=0.68); or —C(=O)—X, where X is hydrogen (—CHO, $\sigma_p$=0.22), $C_1$-$C_6$ alkyl (for example, —C(=O)$CH_3$, $\sigma_p$=0.50), —$OR^1$ ($\sigma_p$≈0.4), or —$NR^2R^3$ (for example, —C(=O)$NH_2$, $\sigma_p$=0.36), wherein each of $R^0$, $R^1$, $R^2$, and $R^3$ may each independently be hydrogen, $C_1$-$C_6$ alkyl, $C_5$-$C_7$ cycloalkyl, phenyl, mono-substituted phenyl, di-substituted phenyl, alkylene glycol, or polyalkylene glycol, wherein the phenyl substituents may be $C_1$-$C_6$ alkyl or $C_1$-$C_6$ alkoxy. Further suitable electron-withdrawing substituents having Hammett $\sigma_p$ values in the range from about 0.05 to about 0.75 are set forth in "Section 9 Physicochemical Relationships" in Lange's Handbook of Chemistry, 15$^{th}$ ed. J. A. Dean, editor, McGraw Hill, 1999, pp 9.1-9.8, the disclosure of which is incorporated herein by reference. It will be appreciated by those skilled in the art that the subscript "p", when used in connection with the Hammett σ value, refers to the Hammett $\sigma_p$ value as measured when the group is located at the para position of a phenyl ring of a model system, such as a para-substituted benzoic acid model system.

As used herein, the term "polyalkylene glycol" means a substituent having the general structure of —[O—($C_aH_{2a}$)]$_b$—OR", where 'a' and 'b' are each independently integers from 1 to 10, and R" may be H, alkyl, a reactive sub substituent, or a second photochromic material. Non-limiting examples of suitable polyalkylene glycols may be found in U.S. Pat. No. 6,113,814, column 3, lines 30-64, which disclosure is incorporated herein by reference. Non-limiting examples of reactive substituents may be found in paragraphs [0033]-[0040] of U.S. patent application Ser. No. 11/102,280, filed Apr. 8, 2005 (Publication 2006/0226400 A1, which disclosure is incorporated herein by reference.

According to various non-limiting embodiments disclosed herein, the first electron-withdrawing group bonded to the 6-position of the indeno-fused naphthopyran may be an electron-withdrawing group as described and set forth above.

It has been recognized by the inventors that certain substitution at the 13-position may have an effect on the fatigue of the photochromic material. As used herein, the term "fatigue" refers to the degradation over time of the photochromic characteristics of the photochromic material. For example, the saturated optical density and/or performance rating of a photochromic material may be degraded over time due to fatigue. As used herein, the term "saturated optical density", abbreviated "Sat'd OD", is a measurement of the steady state absorbance (i.e., optical density) of the photochromic material under standard conditions as defined in the Examples. As used herein, the term "performance rating" or "PR" is a measurement of the performance of a photochromic material and is calculated by the equation:

Performance Rating=((Sat'd OD)/$T_{1/2}$)×10,000.

Generally, as a photochromic material fatigues, the photochromic material may develop a color, for example, a yellow color, in the ground-state form. Such fatigue of a photochromic material may cause a photochromic article that incorporates the photochromic material to develop an undesirable yellowish color when the photochromic material is in the "clear", ground-state form; and/or may result in a photochromic article that has a weaker (i.e., less intense) color in the colored, activated-state form. It has been observed by the inventors that certain substitution patterns may lead to increased fatigue in the photochromic material, that is, the photochromic character or lifetime of the material may be reduced and yellowing may occur. For example, the inventors have observed that substitution of a hydroxyl group at the 13-position of certain indeno-fused naphthopyran may lead to increased fatigue. Although not meant to be bound by any particular theory, the inventors contemplate that this increase in fatigue of the photochromic material may be due to elimination, oxidation or other degradation pathways.

Therefore, according to various non-limiting embodiments, the photochromic materials disclosed herein may comprise an indeno-fused naphthopyran wherein the substitution at the 13-position does not comprise hydroxyl. Further, according to various non-limiting embodiments, the substitution at the 13-position of the indeno-fused naphthopyran may comprise a geminal dialkyl substitution, for example, although not limiting herein, a geminal dimethyl substitution. As used herein, the term "geminal substitution" means that two groups, which may be the same or different, are substituted at the same carbon atom of the structure, for example, at the 13-position of an indeno-fused naphthopyran. For example, geminal dialkyl substitution means two alkyl groups, such as alkyl groups having from 1-6 carbon atoms, are substituted at the same carbon atom.

Throughout the present disclosure, the term "fade rates" represents a kinetic rate value that may be expressed by measuring the $T_{1/2}$ value of the photochromic material. As used herein, the term "fade rate" is a measurement of the rate at which the photochromic material transforms from the activated colored state to the unactivated clear state. The fade rate for a photochromic material may be measured, for example, by activating a photochromic material to saturation under controlled conditions in a given matrix, measuring its activated steady state absorbance (i.e., saturated optical density) and then determining the length of time it takes for the absorbance of the photochromic material to decrease to one-half the activated steady state absorbance value. As measured in this fashion, the fade rate is designated by $T_{1/2}$, with units of seconds. Thus, when the fade rate is said to be "faster", the photochromic compound changes from the colored activated-state to the clear ground-state at a faster rate. The faster fade rate may be indicated, for example, by a decrease in the value of the $T_{1/2}$ measurement for the photochromic material. That is, as the fade rate becomes faster, the length of time for the absorbance to decrease to one-half the initial activated absorbance value will become shorter. More detailed measurement procedures for determining the $T_{1/2}$ values for the photochromic materials, disclosed herein, are set forth in the Examples below.

It will be appreciated by those skilled in the art that the fade rate of the photochromic material may be dependent on the media into which the photochromic material is incorporated. As used herein, the term "incorporated" when used in relation to a photochromic material in a media means physically and/or chemically combined with. In the present disclosure, all photochromic performance data, including fade rate values, as denoted by the $T_{1/2}$ values, and bathochromic shift values, disclosed herein are measured using a standard protocol involving incorporation of the photochromic material into a polymer test chip comprising a methacrylate polymer, unless specifically noted otherwise. Photochromic performance testing and the standard protocol for formation of the polymer test chip, which incorporates the photochromic materials of the various non-limiting embodiments of the present disclosure, are disclosed in greater detail in the Examples section of the present disclosure. One skilled in the art will recognize that although exact values for fade rates and other photochromic performance data, such as, for example, bathochromic shift data, may vary depending on the media of incorporation, the photochromic performance data disclosed herein may be illustrative of relative rates and shifts to be expected for the photochromic material when incorporated in other media.

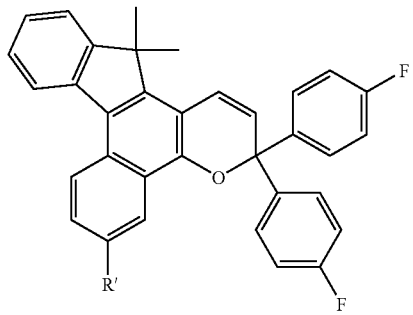

Structure (A)
1a R' = COOCH$_3$
1b R' = H
2 R' = CN

With referenced to Structure (A) and according to certain non-limiting embodiments disclosed herein, the photochromic materials having an electron-withdrawing group at the 6-position of the indeno-fused naphthopyran may have a fade rate that is faster than a comparable indeno-fused naphthopyran without an electron-withdrawing group at the 6-position thereof. For example and with reference to Structure (A), compound 1a, in one specific non-limiting embodiment of the photochromic material, R' is an electron-withdrawing group at the 6-position of the indeno-fused naphthopyran comprising a methoxycarbonyl group (i.e., —C(=O)—X, where X is —OR$^1$ with R$^1$=CH$_3$) and the photochromic material has a fade rate $T_{1/2}$ of 130 seconds. In contrast and with reference to Structure (A), compound 1b, a comparable photochromic material comprising an indeno-fused naphthopyran having R' as a hydrogen at the 6-position (i.e., without the electron-withdrawing group at the 6-position) has a fade rate $T_{1/2}$ of 395 seconds. Further, the indeno-fused naphthopyran of this specific non-limiting example also has B and B' groups at the 3-position, each comprising 4-fluorophenyl, and the substitution at the 13-position of the indeno-fused naphthopyran is geminal dimethyl.

Referring now to Structure (A), compound 2, in another specific non-limiting example, a photochromic material comprising an indeno-fused naphthopyran having R' as a cyano group at the 6-position has a fade rate $T_{1/2}$ of 52 seconds, in contrast to the similar indeno-fused naphthopyran lacking an electron-withdrawing group at the 6-position (i.e., Structure (A), compound 1b) having a $T_{1/2}$ of 395 seconds. Further, the indeno-fused naphthopyran of this specific non-limiting example also has B and B' groups at the 3-position, each comprising 4-fluorophenyl, and the substitution at the 13-position of the indeno-fused naphthopyran is geminal dimethyl.

In addition to faster fade rates, the photochromic materials according to various non-limiting embodiments disclosed herein may have a performance rating that is increased compared to a similar photochromic material comprising a indeno-fused naphthopyran and a first electron-withdrawing group, and, in certain embodiments, a second electron-withdrawing group, as described herein. Performance ratings typically range from 1 to 100, with higher performance ratings generally being preferred. Referring again to the photochromic materials in Structure (A), compounds 1a and 2, the indeno-fused naphthopyrans having a methoxycarbonyl (compound 1a) or cyano group (compound 2) bonded to the 6-position thereof have performance ratings of 62 and 94 respectively, whereas the performance rating for the comparable 6-unsubstituted indeno-fused naphthopyran (i.e., Structure (A), compound 1b) is 28.

Further, the photochromic material comprising an indeno-fused naphthopyran having an electron-withdrawing group at the 6-position may have a maximum absorbance wavelength that is shifted bathochromically by at least 10 nm compared to the maximum absorbance wavelength of a comparable indeno-fused naphthopyran without an electron-withdrawing group at the 6-position thereof. For example, with reference to Structure (A), compounds 1a and 2 have maximum absorbance wavelengths of 543 nm and 551 nm, respectively, whereas the maximum absorbance wavelength for the comparable 6-unsubstituted indeno-fused naphthopyran (Structure (A), compound 1b is 533 nm.

According to various non-limiting embodiments disclosed herein, in addition to the first electron-withdrawing group bonded to the 6-position of the indeno-fused naphthopyran, the photochromic material may further comprise a second electron-withdrawing group bonded to the 11-position of the indeno-fused naphthopyran, wherein the substitution at the 13-position does not comprise hydroxyl. According to the various non-limiting embodiments, the second electron-withdrawing group may comprise, for example and without limitation: halogen, such as fluoro, chloro, and bromo; perfluoroalkyl or perfluoroalkoxy, where the perfluoroalkyl portion may comprise, for example, trifluoromethyl, and other perfluoroalkyl substituents having the formula $C_nF_{2n+1}$; cyano; —OC(=O)$R^4$; —SO$_2$X; or —C(=O)—X, where X is hydrogen, $C_1$-$C_6$ alkyl, —OR$^5$, or —NR$^6$R$^7$, wherein each of $R^4$, $R^5$, $R^6$, and $R^7$ are independently hydrogen, $C_1$-$C_6$ alkyl, $C_5$-$C_7$ cycloalkyl, phenyl, mono-substituted phenyl, di-substituted phenyl, alkylene glycol, or polyalkylene glycol, wherein the phenyl substituents are $C_1$-$C_6$ alkyl or $C_1$-$C_6$ alkoxy. The first electron-withdrawing group and the second electron-withdrawing group may be the same or different.

According to certain non-limiting embodiments disclosed herein, the first electron-withdrawing group and the second electron-withdrawing group of the photochromic material may each independently be: fluoro, chloro, bromo, cyano, or —C(=O)—OR$^8$, wherein R$^8$ is $C_1$-$C_6$ alkyl, alkylene glycol, or polyalkylene glycol.

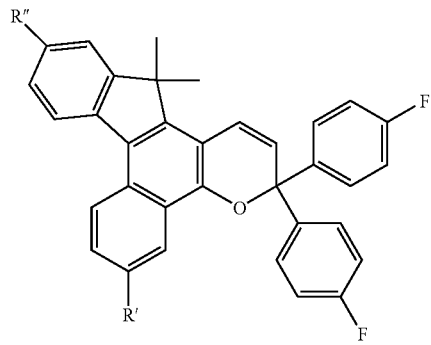

Structure (B)
1b R' and R" = H
3a R' and R" = F
3b R' and R" = Cl
3c R' and R" = CN
3d R' and R" = COOCH$_3$ According to certain non-limiting embodiments disclosed herein, the photochromic materials comprising an indeno-fused naphthopyran having a first electron-withdrawing group and a second electron-withdrawing group, as described and claimed herein, may have a faster fade rate than a comparable indeno-fused naphthopyran without a first and second electron withdrawing group. For example and with reference to Structure (B), compound 3a, in one specific non-limiting embodiment of the photochromic material, R' is a first electron-withdrawing fluoro group and R" is a second electron-withdrawing fluoro group and the photochromic material has a fade rate $T_{1/2}$ value of 199 seconds. In contrast and with reference to Structure (B), compound 1b, a comparable photochromic material comprising an indeno-fused naphthopyran having R' as a hydrogen and R" as a hydrogen (i.e., without a first electron-withdrawing group and a second electron-withdrawing group) has a fade rate $T_{1/2}$ value of 395 seconds. Further, with reference to Structure (B), compounds 3b, 3c, and 3d corresponding to indeno-fused naphthopyrans, according to other non-limiting embodiments of the photochromic materials, having a first and second electron-withdrawing group comprising chloro groups, cyano groups, and methoxycarbonyl groups, respectively, have fade rate $T_{1/2}$ values of 121 seconds, 30 seconds and 71 seconds, respectively.

In addition, photochromic materials comprising an indeno-fused naphthopyran having a first electron-withdrawing group and a second electron-withdrawing group, as described and claimed herein, may have an increased performance rating and a maximum absorbance wavelength that is bathochromically shifted as compared to a comparable indeno-fused naphthopyran without a first and second electron withdrawing group. For example and with reference to Structure (B), compounds 3a, 3b, 3c, and 3d have performance ratings of 45, 54, 76, and 66, respectively, and maximum absorbance wavelength values of 545 nm, 547 nm, 545 nm, and 541 nm, respectively. In contrast and with reference to Structure (B), compound 1b, a comparable photochromic material comprising an indeno-fused naphthopyran having R' as a hydrogen and R" as a hydrogen (i.e., without a first electron-withdrawing group and a second electron-withdrawing group) has a performance rating of 28 and a maximum absorbance wavelength value of 533 nm.

According to other non-limiting embodiments, the present disclosure provides a photochromic material comprising: an indeno-fused naphthopyran; a first electron-withdrawing group bonded to a carbon on the C ring of the indeno-fused naphthopyran; and a second electron-withdrawing group bonded to the 11-position of the indeno-fused naphthopyran, wherein substitution at the 13-position of the indeno-fused naphthopyran does not comprise a hydroxyl group. According to these non-limiting embodiments, the first electron-withdrawing group and the second electron-withdrawing group on the photochromic material may be the same or different. Further, according to certain non-limiting embodiments wherein the photochromic material comprises a first electron-withdrawing group bonded to a carbon of the C ring and a second electron-withdrawing group bonded to the 11-position, wherein substitution at the 13-position does not comprise hydroxyl, the photochromic material may have a faster fade rate than a comparable photochromic material without a first electron-withdrawing group bonded to a carbon of the C ring and a second electron-withdrawing group bonded to the 11-position thereof.

Other non-limiting embodiments disclosed herein provide a photochromic material comprising: an indeno-fused naphthopyran; a first electron-withdrawing group bonded to the 6-position of the indeno-fused naphthopyran; a second electron-withdrawing group bonded to the 11-position of the indeno-fused naphthopyran; and geminal dialkyl substitution at the 13-position of the indeno-fused naphthopyran, wherein the first electron-withdrawing group and the second electron-withdrawing group may be the same or different. According to certain non-limiting embodiments, the photochromic material having a first electron-withdrawing group bonded to the 6-position, a second electron-withdrawing group bonded to the 11-position, and geminal dialkyl substitution at the 13-position of the indeno-fused naphthopyran may have a faster fade rate and higher performance rating than a comparable photochromic material having geminal dialkyl substitution at the 13-position of the indeno-fused naphthopyran without a first electron-withdrawing group bonded to the 6-position of the indeno-fused naphthopyran and a second electron-withdrawing group bonded to the 11-position of the indeno-fused naphthopyran.

Still other non-limiting embodiments disclosed herein provide a photochromic material comprising: an indeno-fused naphthopyran; a first electron-withdrawing group bonded to the 6-position of the indeno-fused naphthopyran; and a second electron-withdrawing group bonded to the 11-position of the indeno-fused naphthopyran, provided that if the first electron-withdrawing group is a fluoro group, then the second electron-withdrawing group is not a fluoro group. According to certain non-limiting embodiments, the photochromic material having a first electron-withdrawing group bonded to the 6-position of the indeno-fused naphthopyran, and a second electron-withdrawing group bonded to the 11-position of the indeno-fused naphthopyran, wherein the first electron-withdrawing group and the second electron-withdrawing group are not both fluoro groups, may have a faster fade rate than a comparable photochromic material without a first electron-withdrawing group bonded to the 6-position of the indeno-fused naphthopyran, and a second electron-withdrawing group bonded to the 11-position of the indeno-fused naphthopyran, wherein the first electron-withdrawing group and the second electron-withdrawing group are not both fluoro groups.

According to any of the various non-limiting embodiments of the photochromic materials described above, the first electron-withdrawing group may be halogen, such as fluoro, chloro, and bromo; perfluoroalkyl or perfluoroalkoxy, where the perfluoroalkyl portion may comprise, for example, trifluoromethyl, and other perfluoroalkyl portion having the formula $C_nF_{2n+1}$; cyano; —OC(=O)$R^0$; —SO$_2$X; or —C(=O)—X, where X is hydrogen, $C_1$-$C_6$ alkyl, —OR$^1$, or —NR$^2$R$^3$, wherein each of R$^0$, R$^1$, R$^2$, and R$^3$ are independently hydrogen, $C_1$-$C_6$ alkyl, $C_5$-$C_7$ cycloalkyl, phenyl, mono-substituted phenyl, di-substituted phenyl, alkylene glycol, or polyalkylene glycol, wherein the phenyl substituents are $C_1$-$C_6$ alkyl or $C_1$-$C_6$ alkoxy.

Further, according to any of the various non-limiting embodiments of the photochromic material comprising a first and a second electron-withdrawing group described above, the second electron-withdrawing group, which may be the same or different from the first electron-withdrawing group, may be halogen, such as fluoro, chloro, and bromo; perfluoroalkyl or perfluoroalkoxy, where the perfluoroalkyl portion may comprise, for example, trifluoromethyl, and other perfluoroalkyl portion having the formula $C_nF_{2n+1}$; cyano; —OC(=O)R$^4$; —SO$_2$X; or —C(=O)—X, where X is hydrogen, $C_1$-$C_6$ alkyl, —OR$^5$, or —NR$^6$R$^7$, wherein each of R$^4$, R$^5$, R$^6$, and R$^7$ are independently hydrogen, $C_1$-$C_6$ alkyl, $C_5$-$C_7$ cycloalkyl, phenyl, mono-substituted phenyl, di-substituted phenyl, alkylene glycol, or polyalkylene glycol, wherein the phenyl substituents are $C_1$-$C_6$ alkyl or $C_1$-$C_6$ alkoxy. In other non-limiting embodiments, the first electron-withdrawing group and the second electron-withdrawing group are each independently, the same or different, fluoro, chloro, bromo, cyano, or —C(=O)—OR$^8$, wherein R$^8$ is $C_1$-$C_6$ alkyl, alkylene glycol, or polyalkylene glycol.

The photochromic materials according to any of the non-limiting embodiments described herein comprising an indeno-fused naphthopyran and a first electron-withdrawing group and, in certain non-limiting embodiments, a second electron-withdrawing group, may have at least one of (i) a closed-form absorption spectrum for electromagnetic radiation wherein the longest wavelength of absorbance is bathochromically shifted as compared to the closed-form absorption spectrum for electromagnetic radiation of a photochromic material comprising a comparable indeno-fused naphthopyran without a first electron-withdrawing group and, in certain non-limiting embodiments, a second electron-withdrawing group; and (ii) an open-form absorption spectrum for electromagnetic radiation that is bathochromically shifted as compared to an open-form absorption spectrum for electromagnetic radiation or a photochromic material comprising a comparable indeno-fused naphthopyran without a first electron-withdrawing group and, in certain non-limiting embodiments, a second electron-withdrawing group. As used herein, the term "bathochromically shifted" means having an absorption spectrum for electromagnetic radiation that is shifted to longer wavelength values.

Figure 1G:
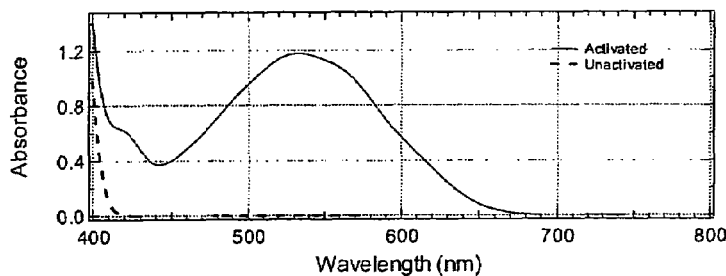
FIG. 1G illustrates the activated and unactivated absorption spectrum within the visible region of a conventional photochromic compound.
Figure 1G:
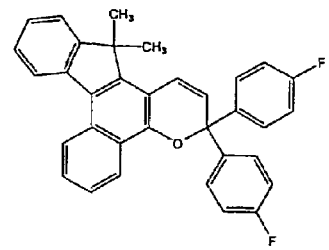

For example, referring to FIGS. 1A-1F, the absorption spectra show both the unactivated and activated absorption spectra within the visible region of the electromagnetic spectrum for indeno-fused naphthopyrans having a first electron-withdrawing group in the 6-position thereof and, in certain non-limiting embodiments, a second electron-withdrawing group in the 11-position thereof according to various non-limiting embodiment disclosed herein. Absorption spectrum of FIG. 1G shows the absorption spectra within the visible region for a comparable photochromic material comprising an indeno-fused naphthopyran without a first electron-withdrawing group and a second electron-withdrawing group. As can be seen in the absorption spectra of FIGS. 1A-1F, the activated, open form absorption spectra for the photochromic materials according to certain non-limiting embodiments of the present disclosure are bathochromically shifted—that is, the absorption spectra of the activated forms are displaced toward longer wavelengths—as compared to the activated absorption spectrum in FIG. 1G.

As discussed above, a bathochromic shifts of the activated form absorption spectrum for visible light for the photochromic materials of the present disclosure provide for photochromic materials (and consequently photochromic articles and devices, etc.) having a bluer color compared to conventional photochromic materials (i.e., the photochromic material absorbs visible light of a longer "redder" wavelength and transmits light of a shorter "bluer" wavelength). Thus, formulations comprising the resulting photochromic materials of the present disclosure may therefore have a more neutral color in the activated form.

In addition, referring now to FIGS. 2A-2F, the absorption spectra show both the unactivated and activated absorption spectra within the ultraviolet region of the electromagnetic spectrum for indeno-fused naphthopyrans having a first electron-withdrawing group in the 6-position thereof and, in certain non-limiting embodiments, a second electron-withdrawing group in the 11-position thereof according to various non-limiting embodiment disclosed herein. Absorption spectrum 2G shows the absorption spectra within the ultraviolet region for a comparable photochromic material comprising an indeno-fused naphthopyran without a first electron-withdrawing group and a second electron-withdrawing group. As can be seen in the absorption spectra of FIGS. 2A-2F, the unactivated closed form absorption spectra for the photochromic material according to certain non-limiting embodiments of the present disclosure are bathochromically shifted—that is, the absorption spectra of the unactivated forms are displaced toward longer wavelengths—as compared to the activated absorption spectrum in FIG. 2G.

Figure 2A:
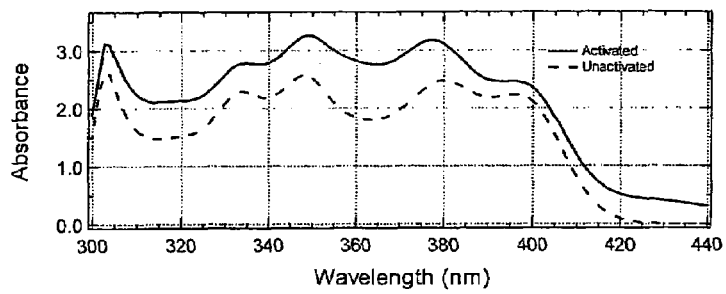
FIGS. 2A, 2B, 2C, 2D, 2E, and 2F illustrate the activated and unactivated absorption spectra within the ultraviolet region of the electromagnetic spectrum for various non-limiting embodiments of the photochromic materials of the present disclosure (spectra in FIGS. 2E and 2F are recorded at half concentration).
Figure 2A:
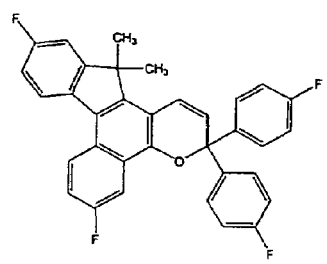
Figure 2B:
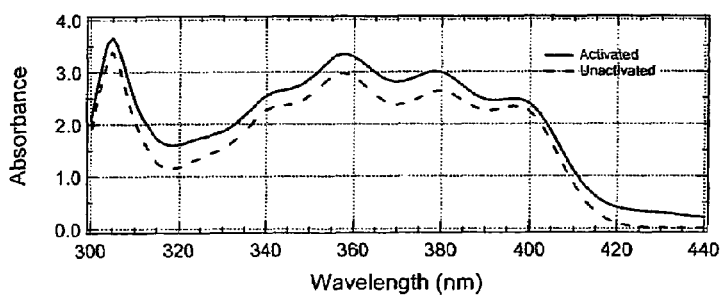
Figure 2B:
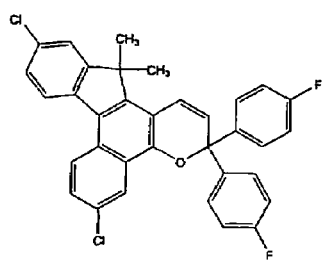
Figure 2C:
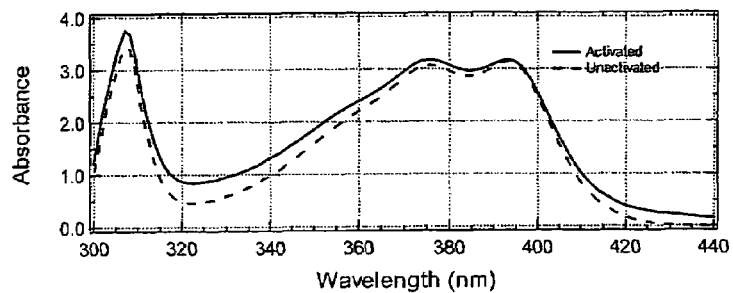
Figure 2C:
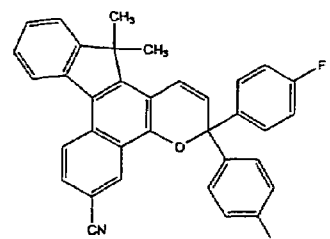
Figure 2D:
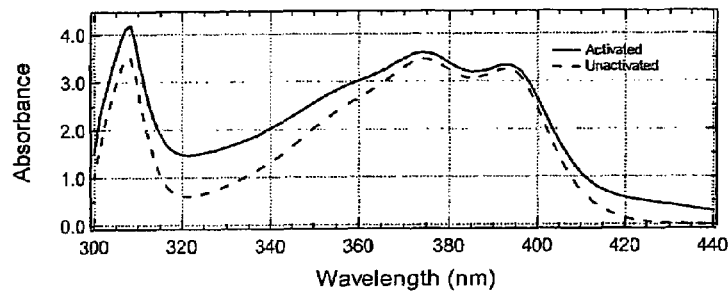
Figure 2D:
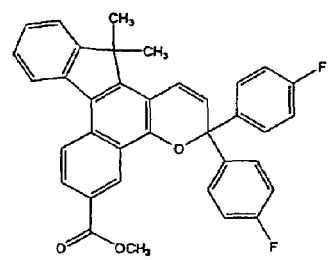
Figure 2E:
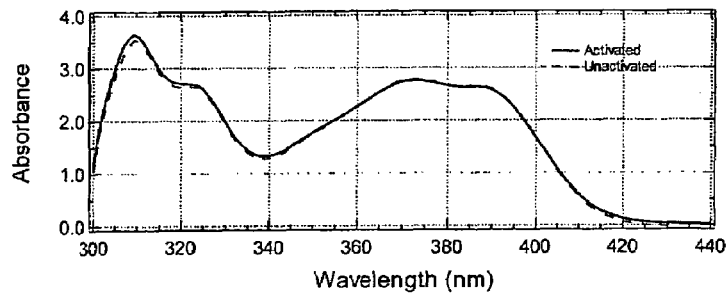
Figure 2E:
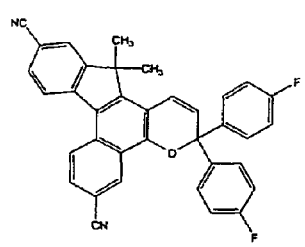
Figure 2F:
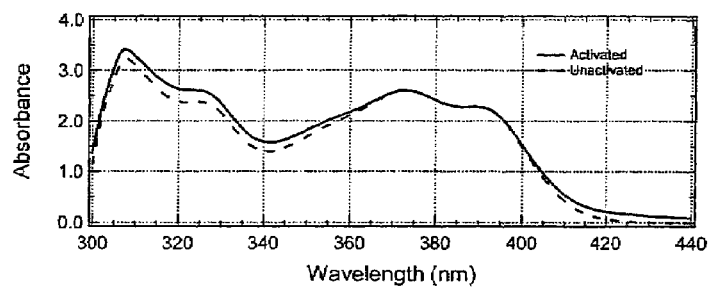
Figure 2F:
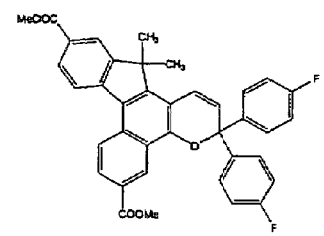
Figure 2G:
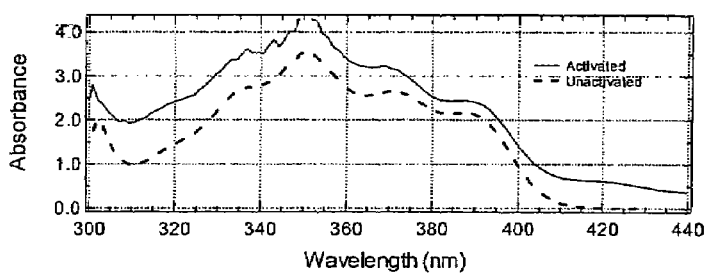
FIG. 2G illustrates the activated and unactivated absorption spectrum within the ultraviolet region of a conventional photochromic compound.
Figure 2G:
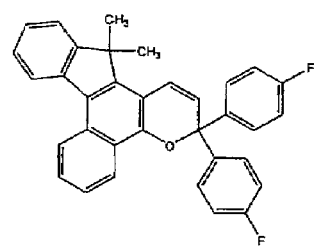

Since absorption spectrum for the unactivated form in FIGS. 2A-2F have increased absorption in the 390 nm to 420 nm range as compared to absorption spectrum of the unactivated form of the comparable photochromic material in FIG. 2G, it is contemplated the photochromic materials from which absorption spectra shown in FIGS. 2A-2F were obtained may be advantageously employed in applications wherein a substantial amount of electromagnetic radiation in the range of 390 nm to 420 nm is shielded or blocked, for example, in applications involving use behind a windshield.

The photochromic materials according to any of the non-limiting embodiments described herein comprising an indeno-fused naphthopyran and a first electron-withdrawing group and, in certain embodiments, a second electron-withdrawing group, may have an open-form absorption spectrum for electromagnetic radiation that is bathochromically shifted by at least about 8 nm compared to an open-form absorption spectrum for electromagnetic radiation of a photochromic material comprising a comparable indeno-fused naphthopyran without a first electron-withdrawing group and, in certain non-limiting embodiments, a second electron-withdrawing group. According to certain non-limiting embodiments of the photochromic materials disclosed herein, the open-form absorption spectrum for electromagnetic radiation is bathochromically shifted by about 8 nm to about 35 nm compared to the comparison photochromic material.

Still further, the photochromic materials according to any of the non-limiting embodiments disclosed herein comprising an indeno-fused naphthopyran and a first electron-withdrawing group and, in certain non-limiting embodiments, a second electron-withdrawing group, may have a closed-form absorption spectrum for electromagnetic radiation that is bathochromically shifted by at least 5 nm compared to the closed-form absorption spectrum for electromagnetic radiation of a photochromic material comprising a comparable indeno-fused naphthopyran without a first electron-withdrawing group and, in certain non-limiting embodiments, a second electron-withdrawing group.

As discussed above, the fade rate of the photochromic materials according to various non-limiting embodiments of the present invention comprising an indeno-fused naphthopyran and a first electron-withdrawing group and, in certain embodiments, further comprising a second electron-withdrawing group, for example, an indeno-fused naphthopyran including a first electron-withdrawing group bonded to the 6-position thereof and, in certain non-limiting embodiments, a second electron-withdrawing group bonded to the 11-position thereof, wherein substitution at the 13-position does not comprise hydroxyl; an indeno-fused naphthopyran including a first electron-withdrawing group bonded to a carbon of the C-ring thereof and a second electron-withdrawing group bonded to the 11-position thereof, wherein substitution at the 13-position does not comprise hydroxyl; an indeno-fused naphthopyran including a first electron-withdrawing group bonded to the 6-position thereof, a second electron-withdrawing group bonded to the 11-position thereof, and geminal dialkyl substitution at the 13-position thereof; or an indeno-fused naphthopyran including a first electron-withdrawing group bonded to the 6-position thereof, a second electron-withdrawing bonded to the 11-position thereof, wherein the first electron-withdrawing group and the second electron withdrawing group are not both fluoro groups; may have faster fade rates, as represented by $T_{1/2}$, as measured in a polymethacrylate chip, compared to a photochromic material comprising an indeno-fused naphthopyran without a first electron-withdrawing group and, according to certain non-limiting embodiments, a second electron-withdrawing group. Further, according to certain non-limiting embodiments disclosed herein wherein the photochromic material comprises a first electron-withdrawing group and, in certain non-limiting embodiments, a second electron-withdrawing group, the fade rate of the photochromic material may be at least 45 seconds faster than the comparable photochromic material without the first electron-withdrawing group and, in certain non-limiting embodiments, the second electron-withdrawing group. According to other non-limiting embodiments, the fade rate of the photochromic material may be from about 45 seconds to about 675 seconds faster that the comparable photochromic material without the first electron-withdrawing group and, in certain non-limiting embodiments, the second electron-withdrawing group.

The photochromic materials according to various non-limiting embodiments of the present disclosure, comprising an indeno-fused naphthopyran, a first electron-withdrawing group and, in certain embodiments, a second electron-withdrawing group may have faster fade rates while still exhibiting acceptable performance ratings, as defined herein. According to certain non-limiting embodiments, the photochromic materials according to the present disclosure may have performance ratings of greater than about 45. According to other non-limiting embodiments, the performance ratings of the photochromic materials according to the present disclosure may be about 45 to about 95.

According to any of the non-limiting embodiments of the photochromic materials described herein, the photochromic materials may further comprise groups B and B' bonded to the 3-position of the indeno-fused naphthopyran wherein the groups B and B' are each independently phenyl, mono-substituted phenyl, or di-substituted phenyl, wherein the substituent on the phenyl are independently an electron-donating group or a third electron-withdrawing group.

According to other non-limiting embodiments, the B and B' groups may each independently be phenyl or 4-substituted phenyl, wherein the substituent on the 4-position of the 4-substituted phenyl may be an electron-donating group, a fluoro group, or a third electron-withdrawing group, as defined below. For example, according to various non-limiting embodiments where the photochromic material may comprise a B and/or B' group where the substituent on the 4-position of the phenyl of at least one of the B and B' groups is fluoro group or an electron-donating group, the electron-donating group may be at least one of $C_1$-$C_6$ alkyl, —$OR^9$, and —$NR^{10}R^{11}$, where $R^9$, $R^{10}$, and $R^{11}$ are each independently hydrogen, $C_1$-$C_6$ alkyl, $C_5$-$C_7$ cycloalkyl, phenyl, mono-substituted phenyl, or di-substituted phenyl, and where the phenyl substituents are $C_1$-$C_6$ alkyl or $C_1$-$C_6$ alkoxy. Alternatively or in addition to, the photochromic material may comprise a B and/or B' group where the substituent on the 4-position of the phenyl of at least one of the B and B' groups is a third electro-withdrawing group. For example, according to certain non-limiting embodiments, the third electron-withdrawing group may be selected from chloro, bromo, perfluoroalkyl, perfluoroalkoxy, cyano, nitro, —OC(═O)Z', —$SO_2$X', or —C(═O)—X', where Z' and X' may each independently be hydrogen, $C_1$-$C_6$ alkyl, —$OR^{12}$, or —$NR^{13}R^{14}$, wherein $R^{12}$, $R^{13}$, and $R^{14}$ are each independently hydrogen, $C_1$-$C_6$ alkyl, $C_5$-$C_7$ cycloalkyl, phenyl, mono-substituted phenyl, di-substituted phenyl, alkylene glycol, or polyalkylene glycol, wherein said phenyl substituents are $C_1$-$C_6$ alkyl or $C_1$-$C_6$ alkoxy.

As discussed above, the photochromic materials according to various non-limiting embodiment disclosed herein may comprise a B and/or B' group that is a 4-substituted phenyl. For example, according to various non-limiting embodiments, the B group may comprise a 4-substituted phenyl where the substituent comprises an electron-donating group and the B' group may comprise a 4-substituted phenyl where the substituent comprises a third electron-withdrawing group. According to other embodiments, although not limiting herein, the B group may be a 4-fluorophenyl group and the B' group may be a 4-substituted phenyl, wherein the substituent in the 4-position is —$NR^{10}R^{11}$. According to these non-limiting embodiments, $R^{10}$ and $R^{11}$ are each independently hydrogen, $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy, or $R^{10}$ and $R^{11}$ come together with the nitrogen atom to form a nitrogen containing ring represented by the following graphic formula II:

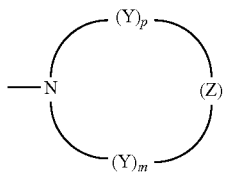

wherein each —Y— is independently chosen for each occurrence from —CH$_2$—, —CH(R$^{15}$)—, —C(R$^{15}$)$_2$—, —CH(aryl)-, —C(aryl)$_2$-, and —C(R$^{15}$)(aryl)-, and Z is —Y—, —O—, —S—, —S(O)—, —SO$_2$—, —NH—, —N(R$^{15}$)—, or —N(aryl)-, wherein each R$^{15}$ is independently C$_1$-C$_6$ alkyl or hydroxy(C$_1$-C$_6$)alkyl, each aryl is independently phenyl or naphthyl, 'm' is an integer 1, 2 or 3, and 'p' is an integer 0, 1, 2, or 3 and when p is 0, Z is —Y—.

According to other non-limiting embodiments, the B group is a 4-fluorophenyl group and the B' group may be 4-morpholinophenyl, 4-piperidinophenyl, 4-(substituted piperidino)phenyl, 4-pyrrolidinophenyl, 4-(substituted pyrrolidino) phenyl, 4-piperazinophenyl, or 4-(substituted pipe4-piperazino)phenyl, wherein the substitution may comprise (C$_1$-C$_6$)alkyl or hydroxy(C$_1$-C$_6$)alkyl, such as, but not limited to, hydroxymethyl. Other embodiments and disclosures wherein the B group may be a 4-fluorophenyl group and the B' group may be a 4-substituted phenyl, wherein the substituent in the 4-position is —NR$^{10}$R$^{11}$ are set forth in U.S. Nonprovisional application Ser. No. 11/314,142 titled "Photochromic Indeno-fused Naphthopyrans," filed concurrently with the present disclosure (Publication 2007/0138448 A1, the disclosure of which is incorporated herein by reference in its entirety.

As previously discussed, according to certain non-limiting embodiments of the photochromic materials comprising an indeno-fused naphthopyran, for example, an indeno-fused naphthopyran including a first electron-withdrawing group bonded to the 6-position thereof and, in certain non-limiting embodiments, a second electron-withdrawing group bonded to the 11-position thereof, wherein substitution at the 13-position does not comprise hydroxyl; or an indeno-fused naphthopyran including a first electron-withdrawing group bonded to a carbon of the C-ring thereof and a second electron-withdrawing group bonded to the 11-position thereof, wherein substitution at the 13-position does not comprise hydroxyl, the photochromic materials may further comprise geminal dialkyl substitution at the 13-position of the indeno-fused naphthopyran. In certain non-limiting embodiments, the geminal dialkyl substitution at the 13-position may comprise geminal dimethyl substitution at the 13-position of the indeno-fused naphthopyran.

According to various non-limiting embodiments disclosed herein, wherein the photochromic material comprises an indeno-fused naphthopyran, a first electron-withdrawing fluoro group in the 6-position thereof, and a second electron-withdrawing fluoro group in the 11-position thereof, wherein the substitution at the 13-position of the indeno-fused naphthopyran does not comprises hydroxyl, the photochromic material may have a fade rate T$_{1/2}$, as measured in a polymethacrylate chip, of at least 50 seconds faster than a photochromic material comprising a comparable indeno-fused naphthopyran without a first electron-withdrawing group bonded to the 6-position thereof and a second-electron withdrawing group bonded to the 11-position thereof. According to other non-limiting embodiments, the photochromic material may have a fade rate T$_{1/2}$, as measured in a polymethacrylate chip, of about 50 seconds to about 200 seconds faster that a photochromic material comprising a comparable indeno-fused naphthopyran without the first electron-withdrawing group and a second electron-withdrawing group.

According to certain non-limiting embodiments, the photochromic materials of the present disclosure comprising: an indeno-fused naphthopyran, a first electron-withdrawing group and, in certain non-limiting embodiments, a second electron withdrawing group; for example, an indeno-fused naphthopyran including a first electron-withdrawing group bonded to the 6-position thereof and, in certain non-limiting embodiments, a second electron-withdrawing group bonded to the 11-position thereof, wherein substitution at the 13-position does not comprise hydroxyl; an indeno-fused naphthopyran including a first electron-withdrawing group bonded to a carbon of the C-ring thereof and a second electron-withdrawing group bonded to the 11-position thereof, wherein substitution at the 13-position does not comprise hydroxyl; or an indeno-fused naphthopyran including a first electron-withdrawing group bonded to the 6-position thereof, a second electron-withdrawing group bonded to the 11-position thereof, and geminal dialkyl substitution at the 13-position thereof, the first electron-withdrawing group may be a fluoro group located at the 6-position of the indeno-fused naphthopyran and the second electron-withdrawing group may be a fluoro group. According to other non-limiting embodiments, wherein the photochromic material comprises an indeno-fused naphthopyran, a first electron-withdrawing group in the 6-position thereof, and a second electron-withdrawing group in the 11-position thereof, if the first electron-withdrawing group is a fluoro group, then the second electron-withdrawing group is not a fluoro group.

Still other non-limiting embodiments disclosed herein provide a photochromic material having a structure schematically represented by structure III below.

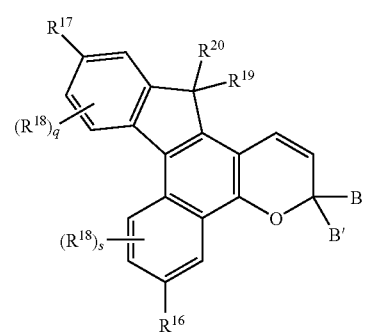

With reference to structure III, R$^{16}$ may be, for example, fluoro, chloro, bromo, perfluoroalkyl, perfluoroalkoxy, cyano, —OC(=O)R$^{21}$, —SO$_2$X, or —C(=O)—X, wherein X is hydrogen, C$_1$-C$_6$ alkyl, —OR$^{22}$, or —NR$^{23}$R$^{24}$, wherein R$^{21}$, R$^{22}$, R$^{23}$, and R$^{24}$ are each independently hydrogen, C$_1$-C$_6$ alkyl, C$_5$-C$_7$ cycloalkyl, phenyl, mono-substituted phenyl, di-substituted phenyl, alkylene glycol, or polyalkylene glycol, wherein said phenyl substituents are C$_1$-C$_6$ alkyl or C$_1$-C$_6$ alkoxy.

R$^{17}$ may be, for example: hydrogen, fluoro, chloro, bromo, perfluoroalkyl, perfluoroalkoxy, cyano, —OC(=O)R$^{25}$, —SO$_2$X, or —C(=O)—X, wherein X is hydrogen, C$_1$-C$_6$ alkyl, —OR$^{26}$, or —NR$^{27}$R$^{28}$, wherein R$^{25}$, R$^{26}$, R$^{27}$, and R$^{28}$ may each be independently chosen for each occurrence from: hydrogen, C$_1$-C$_6$ alkyl, C$_5$-C$_7$ cycloalkyl, phenyl, mono-substituted phenyl, di-substituted phenyl, alkylene glycol, or polyalkylene glycol, wherein said phenyl substituents are C$_1$-C$_6$ alkyl or C$_1$-C$_6$ alkoxy.

Further, according to structure III, 's' may be an integer ranging from 0 to 3, 'q' may be an integer ranging from 0 to 3, and each R$^{18}$ may be independently, for each occurrence: hydrogen; fluoro; chloro; C$_1$-C$_6$ alkyl; C$_3$-C$_7$ cycloalkyl; substituted or unsubstituted phenyl; —OR$^{29}$ or —OC(=O)R$^{29}$, wherein R$^{29}$ may be, for example, hydrogen, C$_1$-C$_6$ alkyl, phenyl(C$_1$-C$_3$)alkyl, mono(C$_1$-C$_6$)alkyl substituted phenyl (C$_1$-C$_3$)alkyl, mono(C$_1$-C$_6$)alkoxy substituted phenyl(C$_1$-C$_3$)alkyl, (C$_1$-C$_6$)alkoxy(C$_2$-C$_4$)alkyl, C$_3$-C$_7$ cycloalkyl, or mono(C$_1$-C$_4$)alkyl substituted C$_3$-C$_7$ cycloalkyl, and said phenyl substituents are C$_1$-C$_6$ alkyl or C$_1$-C$_6$ alkoxy; a monosubstituted phenyl, said phenyl having a substituent located at the para position, wherein the substituent may be: a dicarboxylic acid residue or derivative thereof, a diamine residue or derivative thereof, an amino alcohol residue or derivative thereof, a polyol residue or a derivative thereof, —CH$_2$—, —(CH$_2$)$_t$—, or —[O—(CH$_2$)$_t$]$_k$—, wherein 't' is the integer 2, 3, 4, 5 or 6 and 'k' is an integer from 1 to 50, the substituent being connected to an aryl group on another photochromic material; —N(R$^{30}$)R$^{31}$, wherein R$^{30}$ and R$^{31}$ may each independently be, for example, hydrogen, C$_1$-C$_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, C$_1$-C$_8$ alkylaryl, C$_3$-C$_{20}$ cycloalkyl, C$_4$-C$_{20}$ bicycloalkyl, C$_5$-C$_{20}$ tricycloalkyl or (C$_1$-C$_6$)alkoxy(C$_1$-C$_6$)alkyl, wherein said aryl group may be phenyl or naphthyl, or R$^{30}$ and R$^{31}$ may come together with the nitrogen atom to form a C$_3$-C$_{20}$ hetero-bicycloalkyl ring or a C$_4$-C$_{20}$ hetero-tricycloalkyl ring; a nitrogen containing ring represented by the following graphic formula IVA:

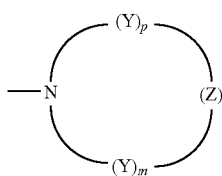

IVA wherein each —Y— may be independently chosen for each occurrence from —CH$_2$—, —CH(R$^{32}$)—, —C(R$^{32}$)$_2$—, —CH(aryl)-, —C(aryl)$_2$-, and —C(R$^{32}$)(aryl)-, and Z may be —Y—, —O—, —S—, —S(O)—, —SO$_2$—, —NH—, —N(R$^{32}$)—, or —N(aryl)-, wherein each R$^{32}$ may independently be C$_1$-C$_6$ alkyl or hydroxy(C$_1$-C$_6$)alkyl, each aryl may independently be phenyl or naphthyl, 'm' is an integer 1, 2 or 3, and 'p' is an integer 0, 1, 2, or 3 provided that if p is 0, Z is —Y—; a group represented by one of the following graphic formulae IVB or IVC:

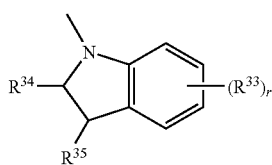

IVB

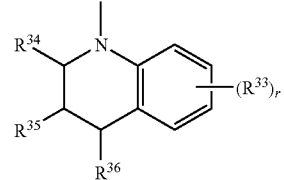

IVC wherein R$^{34}$, R$^{35}$, and R$^{36}$ may each independently be, for example: hydrogen, C$_1$-C$_6$ alkyl, phenyl, or naphthyl, or the groups R$^{34}$ and R$^{35}$ together may form a ring of 5 to 8 carbon atoms and each R$^{33}$ may be independently for each occurrence chosen from C$_1$-C$_6$ alkyl, C$_1$-C$_6$ alkoxy, fluoro or chloro and 'r' is an integer 0, 1, 2, or 3; and unsubstituted, mono-, or di-substituted C$_4$-C$_{18}$ spirobicyclic amine, or unsubstituted, mono-, and di-substituted C$_4$-C$_{18}$ spirotricyclic amine, wherein said substituents may independently be, for example, aryl, C$_1$-C$_6$ alkyl, C$_1$-C$_6$ alkoxy, or phenyl(C$_1$-C$_6$)alkyl; or an R$^{18}$ group in the 6-position of the indeno-fused naphthopyran and an R$^{18}$ group in the 7-position of the indeno-fused naphthopyran together may form a group represented by one of IVD or IVE:

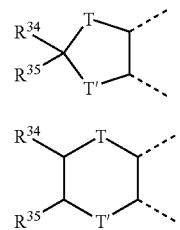

IVD

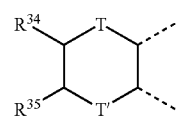

IVE wherein T and T' may each independently be, for example, oxygen or the group —NR$^{30}$—, where R$^{30}$, R$^{34}$, and R$^{35}$ may be as set forth above.

Still further, with reference to structure III, R$^{19}$ and R$^{20}$ may each independently be, for example: hydrogen; C$_1$-C$_6$ alkyl; C$_3$-C$_7$ cycloalkyl; allyl; substituted or unsubstituted phenyl; substituted or unsubstituted benzyl; chloro; fluoro; the group —C(=O)W, wherein W may be hydrogen, hydroxy, C$_1$-C$_6$ alkyl, C$_1$-C$_6$ alkoxy, the unsubstituted, monoor di-substituted aryl groups phenyl or naphthyl, phenoxy, mono- or di-(C$_1$-C$_6$)alkoxy substituted phenoxy, mono- or di-(C$_1$-C$_6$)alkoxy substituted phenoxy, amino, mono(C$_1$-C$_6$) alkylamino, di(C$_1$-C$_6$)alkylamino, phenylamino, mono- or di-(C$_1$-C$_6$)alkyl substituted phenylamino, or mono- or di-(C$_1$-C$_6$)alkoxy substituted phenylamino; —OR$^{37}$, wherein R$^{37}$ may be, for example, C$_1$-C$_6$ alkyl, phenyl(C$_1$-C$_3$)alkyl, mono(C$_1$-C$_6$)alkyl substituted phenyl(C$_1$-C$_3$)alkyl, mono (C$_1$-C$_6$)alkoxy substituted phenyl(C$_1$-C$_3$)alkyl, C$_1$-C$_6$ alkoxy (C$_2$-C$_4$)alkyl, C$_3$-C$_7$ cycloalkyl, mono(C$_1$-C$_4$)alkyl substituted C$_3$-C$_7$ cycloalkyl, C$_1$-C$_6$ chloroalkyl, C$_1$-C$_6$ fluoroalkyl, allyl, or the group —CH(R$^{38}$)Y''', wherein R$^{38}$ may be, for example, hydrogen or C$_1$-C$_3$ alkyl and Y''' may be CN, CF$_3$, or COOR$^{39}$, wherein R$^{39}$ may be, for example, hydrogen or C$_1$-C$_3$ alkyl, or R$^{37}$ is the group, —C(=O)W', wherein W' may be, for example, hydrogen, C$_1$-C$_6$ alkyl, C$_1$-C$_6$ alkoxy, the unsubstituted, mono- or di-substituted aryl groups phenyl or naphthyl, phenoxy, mono- or di-(C$_1$-C$_6$)alkyl substituted phenoxy, mono- or di-(C$_1$-C$_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, wherein each of said phenyl, or naphthyl group substituents may be independently $C_1$-$C_6$ alkyl or $C_1$-$C_6$ alkoxy; or a mono-substituted phenyl, said phenyl having a substituent located at the para position, wherein the substituent may be, for example: a dicarboxylic acid residue or derivative thereof, a diamine residue or derivative thereof, an amino alcohol residue or derivative thereof, a polyol residue or derivative thereof, —$CH_2$—, —($CH_2$)$_t$—, or —[O—($CH_2$)$_t$]$_k$—, wherein 't' is from an integer 2, 3, 4, 5 or 6 and 'k' is an integer from 1 to 50, the substituent being connected to an aryl group on another photochromic material; or $R^{19}$ and $R^{20}$ together may form an oxo group, a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annulated with 0, 1 or 2 benzene rings.

With reference still to structure III, B and B' may each independently be, for example: an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl, wherein each of the phenyl, aryl and heteroaromatic substituents may each independently be, for example: hydroxyl, a group —C(=O)$R^{40}$, wherein $R^{40}$ may be, for example, —O$R^{41}$, —N($R^{42}$)$R^{43}$, piperidino, or morpholino, wherein $R^{41}$ may be, for example, allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, said halo substituent may be chloro or fluoro, $R^{42}$ and $R^{43}$ may each independently be, for example, $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy; an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —$CH_2$—, —($CH_2$)$_t$—, or —[O—($CH_2$)$_t$]$_k$—, wherein 't' is an integer 2, 3, 4, 5 or 6 and 'k' is an integer from 1 to 50, the substituent being connected to an aryl group on another photochromic material; a group represented by one of:

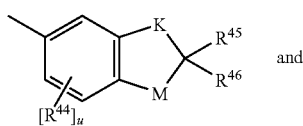 and

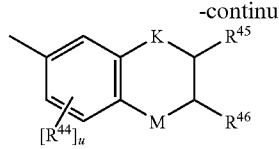

wherein K may be —$CH_2$— or —O—, and M may be —O— or substituted nitrogen, provided that when M is substituted nitrogen, K is —$CH_2$—, the substituted nitrogen substituents may be hydrogen, $C_1$-$C_{12}$ alkyl, or $C_1$-$C_{12}$ acyl, each $R^{44}$ may independently be chosen for each occurrence from $C_1$-$C_{12}$ alkyl, $C_1$-$C_{12}$ alkoxy, hydroxy, and halogen, $R^{45}$ and $R^{46}$ each may independently be, for example, hydrogen or $C_1$-$C_{12}$ alkyl, and 'u' is an integer ranging from 0 to 2; or a group represented by:

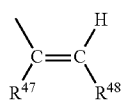

wherein $R^{47}$ may be, for example, hydrogen or $C_1$-$C_{12}$ alkyl, and $R^{48}$ may be, for example, an unsubstituted, mono-, or di-substituted group chosen from naphthyl, phenyl, furanyl, and thienyl, wherein the substituents are $C_1$-$C_{12}$ alkyl, $C_1$-$C_{12}$ alkoxy, or halogen; or B and B' taken together may form one of a fluoren-9-ylidene, mono-, or di-substituted fluoren-9-ylidene, each of said fluoren-9-ylidene substituents may independently be chosen from $C_1$-$C_{12}$ alkyl, $C_1$-$C_{12}$ alkoxy, and halogen.

According to certain non-limiting embodiments, the photochromic material of structure III exhibits a faster fade rate than a comparable photochromic material without a group $R^{16}$ attached in the 6-position thereof.

In certain non-limiting embodiments of structure III, B is 4-fluorophenyl and B' comprises a 4-substituted phenyl, wherein the substituent in the 4-position may be —N$R^{10}R^{11}$, wherein $R^{10}$ and $R^{11}$ may each independently be, for example, hydrogen, $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy, or $R^{10}$ and $R^{11}$ may come together with the nitrogen atom to form a nitrogen containing ring represented by graphic formula II:

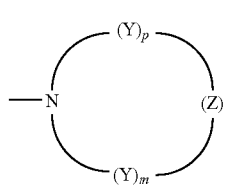

II wherein each —Y— may independently be chosen for each occurrence from —$CH_2$—, —CH($R^{15}$)—, —C($R^{15}$)$_2$—, —CH(aryl)-, —C(aryl)$_2$-, and —C($R^{15}$)(aryl)-, and Z may be —Y—, —O—, —S—, —S(O)—, —$SO_2$—, —NH—, —N($R^{15}$)—, or —N(aryl)-, wherein each $R^{15}$ may independently be $C_1$-$C_6$ alkyl, or hydroxy($C_1$-$C_6$)alkyl, each aryl may independently be phenyl or naphthyl, 'm' is an integer 1, 2 or 3, and 'p' is an integer 0, 1, 2, or 3 and when p is 0, Z is —Y—. According to other non-limiting embodiment of the photochromic material B' comprises 4-morpholinophenyl, 4-piperidinophenyl, 4-(substituted piperidino)phenyl, 4-pyrrolidinophenyl, 4-(substituted pyrrolidino)phenyl, 4-piperazinophenyl, or 4-(substituted piperazino)phenyl, wherein the substitution may comprise $(C_1$-$C_6)$alkyl or hydroxy$(C_1$-$C_6)$alkyl, such as, but not limited to, hydroxymethyl.

According to certain non-limiting embodiments wherein the photochromic material is represented by structure III, $R^{16}$ may be fluoro, $R^{17}$ may be fluoro, and $R^{19}$ and $R^{20}$ may each independently be $C_1$-$C_6$ alkyl. In certain non-limiting embodiments, B may be 4-fluorophenyl and B' may comprise a 4-substituted phenyl, wherein the substituent in the 4position is —$NR^{10}R^{11}$, wherein $R^{10}$ and $R^{11}$ may each independently be hydrogen, $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy, or $R^{10}$ and $R^{11}$ come together with the nitrogen atom to form a nitrogen containing ring represented by graphic formula II:

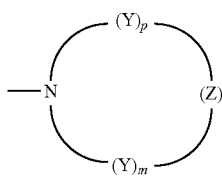

II wherein each —Y— may independently chosen be for each occurrence from —$CH_2$—, —$CH(R^{15})$—, —$C(R^{15})_2$—, —CH(aryl)-, —C(aryl)$_2$-, and —$C(R^{15})$(aryl)-, and Z may be —Y—, —O—, —S—, —S(O)—, —$SO_2$—, —NH—, —$N(R^{15})$—, or —N(aryl)-, wherein each $R^{15}$ may independently be $C_1$-$C_6$ alkyl, or hydroxy$(C_1$-$C_6)$alkyl, each aryl may be independently phenyl or naphthyl, 'm' is an integer 1,2 or 3, and 'p' is an integer 0,1,2, or 3 and when p is 0, Z is —Y—. According to other non-limiting embodiment of the photochromic material B' comprises 4-morpholinophenyl, 4-piperidinophenyl, 4-(substituted piperidino)phenyl, 4-pyrrolidinophenyl, 4-(substituted pyrrolidino)phenyl, 4-piperazinophenyl, or 4-(substituted piperazino)phenyl, wherein the substitution may comprise $(C_1$-$C_6)$alkyl or hydroxy$(C_1$-$C_6)$alkyl, such as, but not limited to, hydroxymethyl.

Certain other non-limiting embodiments of the photochromic materials of the present disclosure may be represented by their chemical name, as determined, at least in part, by the IUPAC system of nomenclature. Photochromic materials contemplated by the present disclosure include:
(a) 3,3-di(4-methoxyphenyl)-6,11-difluoro-13,13-dimethyl-3H,13H-indeno[2',3':3,4]naphtho[1,2-b]pyran;
(b) 3-(4-fluorophenyl)-3-(4-methoxyphenyl)-6,11-difluoro-13,13-dimethyl-3H,13H-indeno[2',3':3,4]naphtho[1,2-b]pyran;
(c) 3-(4-fluorophenyl)-3-(4-piperidinophenyl)-6,11-difluoro-13,13-dimethyl-3H,13H-indeno[2',3':3,4]naphtho[1,2-b]pyran;
(d) 3-(4-methoxyphenyl)-3-(4-morpholinophenyl)-6,11-difluoro-13,13-dimethyl-3H,13H-indeno[2',3':3,4]naphtho[1,2-b]pyran;
(e) 3-(4-fluorophenyl)-3-(4-morpholinophenyl)-6,11-difluoro-13,13-dimethyl-3H,13H-indeno[2',3':3,4]naphtho[1,2-b]pyran;
(f) 3-(4-methylphenyl)-3-(4-morpholinophenyl)-6,11-difluoro-13,13-dimethyl-3H,13H-indeno[2',3':3,4]naphtho[1,2-b]pyran;
(g) 3-phenyl-3-(4-piperidinophenyl)-6,11-difluoro-13,13-dimethyl-3H,13H-indeno[2',3':3,4]naphtho[1,2-b]pyran;
(h) 3-(4-morpholinophenyl)-3-phenyl-6,11-difluoro-13,13-dimethyl-3H,13H-indeno[2',3':3,4]naphtho[1,2-b]pyran;
(i) 3-(4-fluorophenyl)-3-(4-methoxyphenyl)-6,11-dichloro-13,13-dimethyl-3H,13H-indeno[2',3':3,4]naphtho[1,2-b]pyran;
(j) 3,3-di(4-fluorophenyl)-6,11-dichloro-13,13-dimethyl-3H,13H-indeno[2',3':3,4]naphtho[1,2-b]pyran;
(k) 3-phenyl-3-(4-piperidinophenyl)-6,11-dichloro-13,13-dimethyl-3H,13H-indeno[2',3':3,4]naphtho[1,2-b]pyran;
(l) 3-(4-methoxyphenyl)-3-(5-methylthiophen-2-yl)-6,11-dichloro-13,13-dimethyl-3H,13H-indeno[2',3':3,4]naphtho[1,2-b]pyran;
(m) 3,3-di(4-methoxyphenyl)-6,11-dichloro-13,13-dimethyl-3H,13H-indeno[2',3':3,4]naphtho[1,2-b]pyran;
(n) 3,3-di(4-fluorophenyl)-6-cyano-13,13-dimethyl-3H,13H-indeno[2',3':3,4]naphtho[1,2-b]pyran;
(o) 3,3-di(4-fluorophenyl)-6,11-dicyano-13,13-dimethyl-3H,13H-indeno[2',3':3,4]naphtho[1,2-b]pyran;
(p) 3,3-diphenyl-6,11-dicyano-13,13-dimethyl-3H,13H-indeno[2',3':3,4]naphtho[1,2-b]pyran;
(q) 3,3-di(4-fluorophenyl)-6-methoxycarbonyl-13,13-dimethyl-3H,13H-indeno[2',3':3,4]naphtho[1,2-b]pyran;
(r) 3,3-di(4-fluorophenyl)-6,11-di(methoxycarbonyl)-13,13-dimethyl-3H,13H-indeno[2',3':3,4]naphtho[1,2-b]pyran;
(s) 3,3-di(4-methoxyphenyl)-6,11-di(methoxycarbonyl)-13,13-dimethyl-3H,13H-indeno[2',3':3,4]naphtho[1,2-b]pyran;
(t) 3-(4-morpholinophenyl)-3-phenyl-6-bromo-13,13-dimethyl-3H,13H-indeno[2',3':3,4]naphtho[1,2-b]pyran;
(u) 3-(4-methoxyphenyl)-3-phenyl-6-bromo-13,13-dimethyl-3H,13H-indeno[2',3':3,4]naphtho[1,2-b]pyran; and
(v) 3,3-di(4-fluorophenyl)-6,11-difluoro-13,13-dimethyl-3H,13H-indeno[2',3':3,4]naphtho[1,2-b]pyran.

Figure 3:
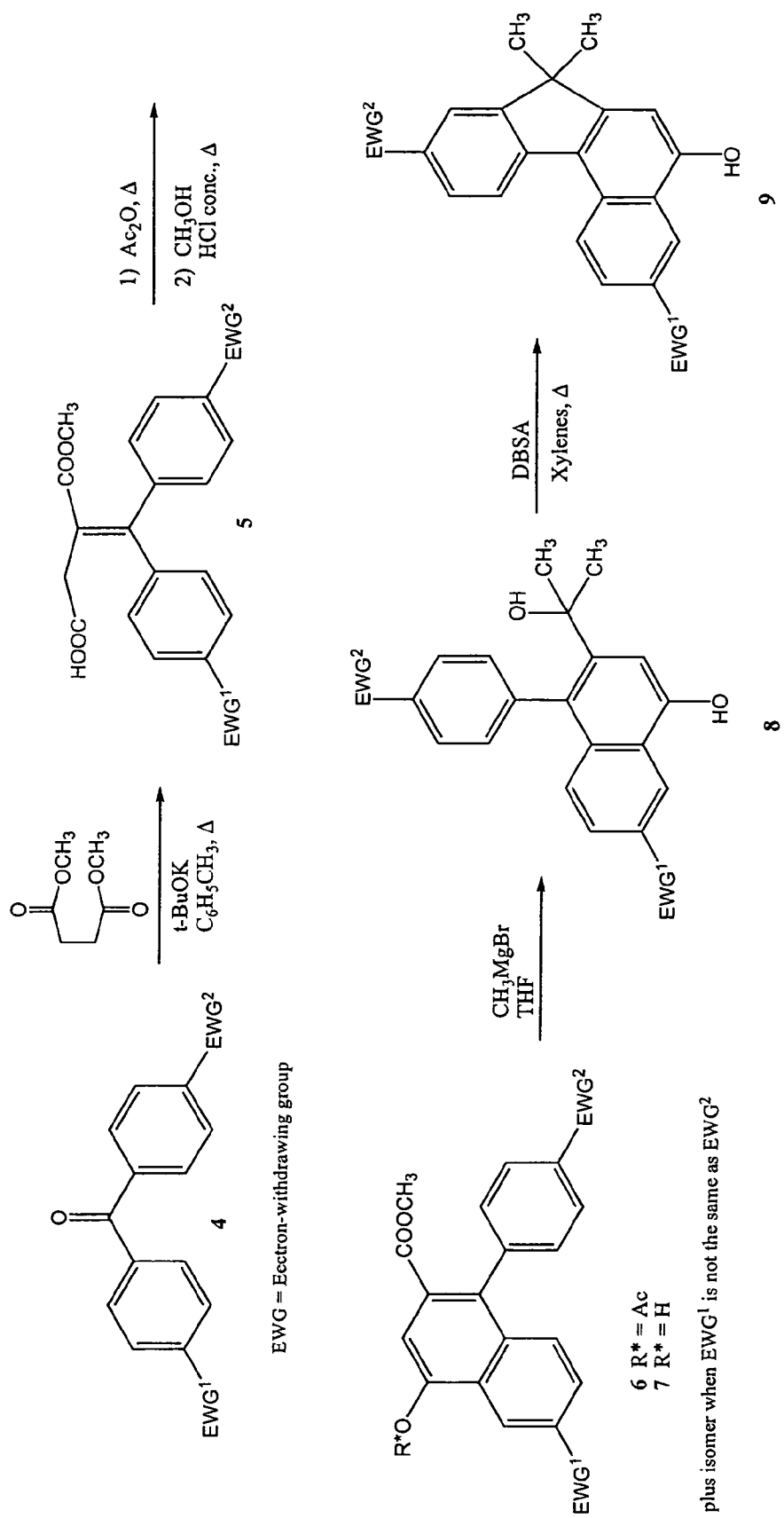
FIG. 3 illustrates a schematic diagram of a reaction scheme for making an intermediate in the synthesis of the photochromic materials according to various non-limiting embodiments disclosed herein.
Figure 4:
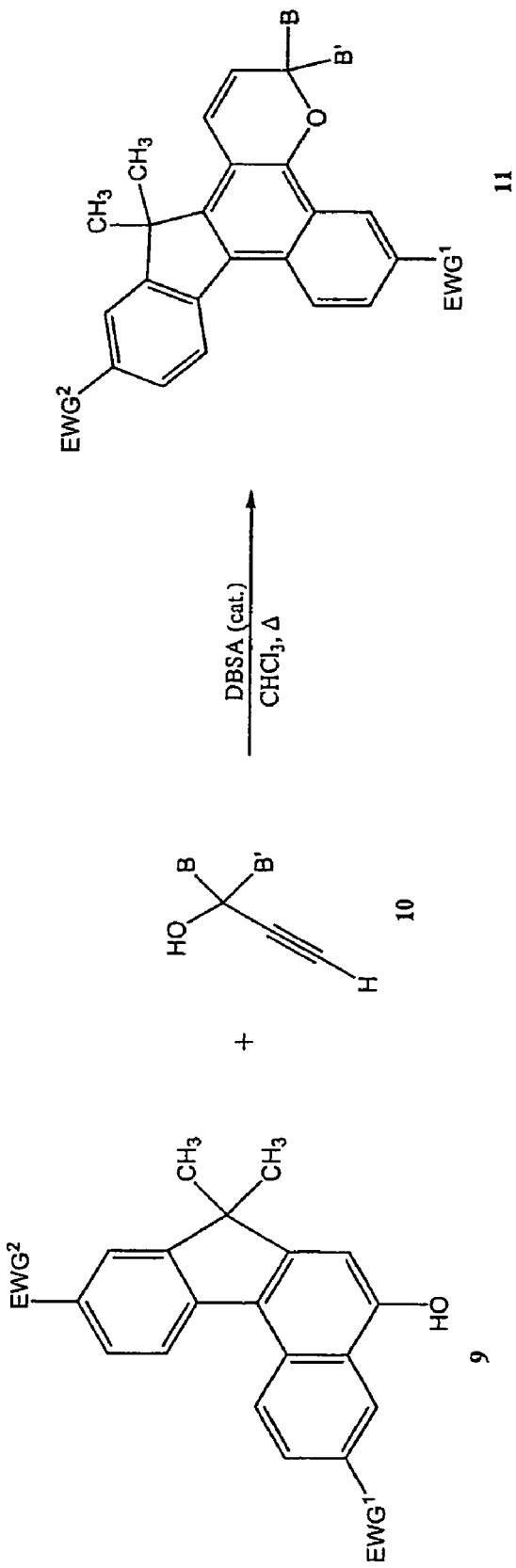
FIG. 4 illustrates a schematic diagram of a reaction scheme for making photochromic materials according to various non-limiting embodiments disclosed herein.

Non-limiting methods of making the photochromic materials of various non-limiting embodiments of present disclosure will now be discussed with reference to FIGS. 3 and 4. FIG. 3 illustrates a reaction scheme for making 7H-benzo[C] fluoren-5-ol compounds having electron-withdrawing groups substituted thereon. The substituted 7H-benzo[C] fluoren-5-ol compounds may then be further reacted, as depicted in FIG. 4 to form photochromic materials comprising a 3H,13H-indeno[2',3':3,4]naphtho[1,2-b]pyran according to various non-limiting embodiments disclosed herein, wherein the indeno-fused naphthopyran has a first electron-withdrawing group bonded to the 6-position thereof and, as depicted in the Figures, a second electron-withdrawing group bonded in the 11-position thereof. It will be appreciated that these reaction schemes are presented for illustration purposes only, and are not intended to be limiting herein. Additional examples of methods of making the photochromic materials according to various non-limiting embodiments disclosed herein are set forth in the Examples.

Referring now to FIG. 3, benzophenone 4 substituted with a first electron-withdrawing group ("$EWG^1$") at the 4-position of the first phenyl ring and a second electron-withdrawing group ("$EWG^2$") at the 4'-position of the second phenyl ring undergoes a Stobbe condensation with dimethyl succinate to give carboxylic acid 5, as a mixture of double bond isomers (when $EWG^1$ is not the same as $EWG^2$). The first electron-withdrawing group and the second electron-withdrawing group of benzophenone 4 may be the same or different and may have the structures as set forth herein above and in the claims. Carboxylic acid 5 is reacted with acetic anhydride at elevated temperature to produce substituted naphthalene 6, where R* is acetate. The acetate is hydrolyzed to give naphthol 7 (R*=H). The ester of naphthol 7 is reacted with excess methyl magnesium bromide to give diol 8 upon aqueous workup. Diol 8 is cyclized with a sulfonic acid, such as, for example, methane sulfonic acid or dodecylbenzene sulfonic acid ("DBSA"), to give substituted 7H-benzo[C]fluoren-5-ol 9.

Referring now to FIG. 4, the substituted 7H-benzo[C]fluoren-5-ol 9 may be reacted with 2-propyn-1-ol 10, wherein the 1-position of the 2-propyn-1-ol is substituted with groups B and B' as set forth herein. Non-limiting methods of synthesizing substituted 2-propyn-1-ols, suitable for use in the synthesis of various non-limiting embodiments disclosed herein, are described, for example, in U.S. Pat. No. 5,458,814 at col. 4, line 11 to col. 5, line 9 and at step 1 of Examples 1, 4,-6, 11, 12, and 13 and U.S. Pat. No. 5,645,767 at col. 5, line 12 to col. 6, line 30, which disclosures are incorporated herein by reference, The condensation of 9 and 10 is catalyzed with a sulfonic acid, such as, for example, DBSA, and affords a 3H,13H-indeno[2',3':3,4]naphthor[1,2-b]pyran 11, according to certain non-limiting embodiments of the present disclosure having a first electron-withdrawing group bonded to the 6-position thereof and a second electron-withdrawing group bonded to the 11-position thereof One skilled in the art will recognize that various modifications of reagents and/or reaction conditions may be made to the reaction schemes set forth in FIGS. 3 and 4 to afford the various non-limiting embodiments of the photochromic materials comprising substituted indeno-fused naphthopyrans, as set forth and claimed herein, and that such modifications are within the scope of the invention of the present disclosure.

The photochromic materials of the present disclosure, for example photochromic materials comprising an indeno-fused naphthopyran and a first electron-withdrawing group and, in certain non-limiting embodiments, a second electron-withdrawing group, as set forth herein, may be used in those applications in which photochromic materials may be employed, such as, optical elements, for example, an ophthalmic element, a display element, a window, a mirror, an active liquid crystal cell element, or a passive liquid crystal cell element. As used herein, the term "optical" means pertaining to or associated with light and/or vision. As used herein, the term "ophthalmic" means pertaining to or associated with the eye and vision. As used herein, the term "display" means the visible or machine-readable representation of information in words, numbers, symbols, designs or drawings. Non-limiting examples of display elements include screens, monitors, and security elements, such as security marks. As used herein, the term "window" means an aperture adapted to permit the transmission of radiation therethrough. Non-limiting examples of windows include aircraft and automotive windshields, automotive and aircraft transparencies, e.g., T-roofs, sidelights and backlights, filters, shutters, and optical switches. As used herein, the term "mirror" means a surface that specularly reflects a large fraction of incident light. As used herein, the term "liquid crystal cell" refers to a structure containing a liquid crystal material that is capable of being ordered. One non-limiting example of a liquid crystal cell element is a liquid crystal display.

In certain non-limiting embodiments, the photochromic materials of the present disclosure may be used in an ophthalmic element, such as, corrective lenses, including single vision or multi-vision lenses, which may be either segmented or non-segmented multi-vision lenses (such as, but not limited to, bifocal lenses, trifocal lenses and progressive lenses), non-corrective lenses, a magnifying lens, a protective lens, a visor, goggles, and a lens for an optical instrument, such as a camera or telescope lens. In other non-limiting embodiments, the photochromic materials of the present disclosure may be used in plastic films and sheets, textiles, and coatings.

Further, it is contemplated that the photochromic materials according to various non-limiting embodiments disclosed herein may each be used alone, in combination with other photochromic materials according to various non-limiting embodiments disclosed herein, or in combination with an appropriate complementary conventional photochromic material. For example, the photochromic materials according to various non-limiting embodiments disclosed herein may be used in conjunction with conventional photochromic materials having activated absorption maxima within the range of about 400 to about 800 nanometers. Further, the photochromic materials according to various non-limiting embodiments disclosed herein may be used in conjunction with a complementary conventional polymerizable or a compatiblized photochromic material, such as for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

As discussed above, according to various non-limiting embodiments disclosed herein, the photochromic compositions may contain a mixture of photochromic materials. For example, although not limiting herein, mixtures of photochromic materials may be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

Various non-limiting embodiments disclosed herein provide a photochromic composition comprising an organic material, said organic material being at least one of polymeric material, an oligomeric material and a monomeric material, and a photochromic material according to any of the non-limiting embodiments of set forth above incorporated into at least a portion of the organic material. According to various non-limiting embodiments disclosed herein, the photochromic material may be incorporated into a portion of the organic material by at least one of blending and bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof.

As discussed above, the photochromic compositions according to various non-limiting embodiments disclosed herein may comprise an organic material chosen from a polymeric material, an oligomeric material and/or a monomeric material. Examples of polymeric materials that may be used in conjunction with various non-limiting embodiments disclosed herein include, without limitation: polymers of bis (allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene) dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly($\alpha$-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, e.g., to form interpenetrating network products.

Further, according to various non-limiting embodiments wherein transparency of the photochromic composition is desired, the organic material may be a transparent polymeric material. For example, according to various non-limiting embodiments, the polymeric material may be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other co-polymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly (vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and co-polymers of styrene with methyl methacrylate, vinyl acetate and acrylonitrile. According to one non-limiting embodiment, the polymeric material may be optical resins sold by PPG Industries, Inc. under the CR-designation, such as, for example, CR-307, CR-407, and CR-607.

According to certain specific non-limiting embodiment, the organic material may be a polymeric material chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

Various non-limiting embodiments disclosed herein provide photochromic articles comprising a substrate and a photochromic material according to any of the non-limiting embodiments discussed above connected to or incorporated into a portion of the substrate. As used herein, the term "connected to" means associated with, either directly or indirectly through another material or structure. In one non-limiting embodiment, the photochromic articles of the present disclosure may be an optical element, for example, but not limited to, an ophthalmic element, a display element, a window, a mirror, an active liquid crystal cell element, and a passive liquid crystal cell element. In certain non-limiting embodiments, the photochromic article is an ophthalmic element, for example, but not limited to, corrective lenses, including single vision or multi-vision lenses, which may be either segmented or non-segmented multi-vision lenses (such as, but not limited to, bifocal lenses, trifocal lenses and progressive lenses), non-corrective lenses, a magnifying lens, a protective lens, a visor, goggles, and a lens for an optical instrument.

According to various non-limiting embodiments disclosed herein wherein the substrate of the photochromic article comprises a polymeric material, the photochromic material may be connected to at least a portion of the substrate by incorporating the photochromic material into at least a portion of the polymeric material of the substrate, or at least a portion of the oligomeric or monomeric material from which the substrate is formed. For example, according to one non-limiting embodiment, the photochromic material may be incorporated into the polymeric material of the substrate by the cast-in-place method. Additionally or alternatively, the photochromic material may be incorporated into at least a portion of the polymeric material of the substrate by imbibition. Imbibition and the cast-in-place method are discussed below.

According to other non-limiting embodiments, the photochromic material may be connected to at least a portion of the substrate of the photochromic article as part of an at least partial coating that is connected to at least a portion of a substrate. According to this non-limiting embodiment, the substrate may be a polymeric substrate or an inorganic substrate (such as, but not limited to, a glass substrate). Further, the photochromic material may be incorporated into at least a portion of the coating composition prior to application of the coating composition to the substrate, or alternatively, a coating composition may be applied to the substrate, at least partially set, and thereafter the photochromic material may be imbibed into at least a portion of the coating. As used herein, the terms "set" and "setting" include, without limitation, curing, polymerizing, cross-linking, cooling, and drying.

For example, in one non-limiting embodiment of the present disclosure, the photochromic article may comprise an at least partial coating of a polymeric material connected to at least a portion of a surface thereof. According to this non-limiting embodiment, the photochromic material may be blended and/or bonded with at least a portion of the polymeric material of the at least partial coating.

The at least partial coating comprising a photochromic material may be directly connected the substrate, for example, by directly applying a coating composition comprising a photochromic material to at least a portion of a surface of the substrate, and at least partially setting the coating composition. Additionally or alternatively, the at least partial coating comprising a photochromic material may be connected to the substrate, for example, through one or more additional coatings. For example, while not limiting herein, according to various non-limiting embodiments, an additional coating composition may be applied to at least a portion of the surface of the substrate, at least partially set, and thereafter the coating composition comprising a photochromic material may be applied over the additional coating and at least partially set. Non-limiting methods of applying coatings compositions to substrates are discussed herein below.

Non-limiting examples of additional coatings and films that may be used in conjunction with the photochromic articles disclosed herein include primer or compatiblizing coatings; protective coatings, including transitional coatings, abrasion-resistant coatings and other coating that protect against the effects of polymerization reaction chemicals and/or protect against deterioration due to environmental conditions such as moisture, heat, ultraviolet light, oxygen (e.g., UV-shielding coatings and oxygen barrier-coatings); anti-reflective coatings; conventional photochromic coating; and polarizing coatings and polarizing stretched-films; and combinations thereof.

Non-limiting examples of primer or compatiblizing coatings that may be used in conjunction with various non-limiting embodiments disclosed herein include coatings comprising coupling agents, at least partial hydrolysates of coupling agents, and mixtures thereof. As used herein "coupling agent" means a material having a group capable of reacting, binding and/or associating with a group on a surface. Coupling agents according to various non-limiting embodiments disclosed herein may include organometallics such as silanes, titanates, zirconates, aluminates, zirconium aluminates, hydrolysates thereof and mixtures thereof. As used herein the phrase "at least partial hydrolysates of coupling agents" means that some to all of the hydrolyzable groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating" means a coating that aids in creating a gradient in properties between two coatings. For example, although not limiting herein, a transitional coating may aid in creating a gradient in hardness between a relatively hard coating (such as an abrasion-resistant coating) and a relatively soft coating (such as a photochromic coating). Non-limiting examples of transitional coatings include radiation-cured, acrylate-based thin films as described in U.S. Patent Application Publication 2003/0165686 at paragraphs [0079]-[0173], which are hereby specifically incorporated by reference herein.

As used herein the term "abrasion-resistant coating" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion-resistant coatings include abrasion-resistant coatings comprising organosilanes, organosiloxanes, abrasion-resistant coatings based on inorganic materials such as silica, titania and/or zirconia, and organic abrasion-resistant coatings of the type that are ultraviolet light curable.

Non-limiting examples of antireflective coatings include a monolayer, multilayer coatings of metal oxides, metal fluorides, or other such materials, which may be deposited onto the articles disclosed herein (or onto self supporting films that are applied to the articles), for example, through vacuum deposition, sputtering, etc.

Non-limiting examples of conventional photochromic coatings include, but are not limited to, coatings comprising conventional photochromic materials.

Non-limiting examples of polarizing coatings and polarizing stretched-films include, but are not limited to, coatings (such as those described in U.S. Patent Application Publication No. 2005/0151926), and stretched-films comprising dichroic compounds that are known in the art.

As discussed herein, according to various non-limiting embodiments, an additional at least partial coating or film may be formed on the substrate prior to forming the coating comprising the photochromic material according to various non-limiting embodiments disclosed herein on the substrate. For example, according to certain non-limiting embodiments a primer or compatilibizing coating may be formed on the substrate prior to applying the coating composition comprising the photochromic material. Additionally or alternatively, an additional at least partial coating may be formed on the substrate after forming coating comprising the photochromic material according to various non-limiting embodiments disclosed herein on the substrate, for example, as an overcoating on the photochromic coating. For example, according to certain non-limiting embodiments, a transitional coating may be formed over the coating comprising the photochromic material, and an abrasion-resistant coating may be formed over the transitional coating.

For example, according to one non-limiting embodiment there is provided a photochromic article comprising a substrate (such as, but not limited to a plano-concave or a plano-convex ophthalmic lens substrate), which comprises an abrasion-resistant coating on at least a portion of a surface thereof; a primer or compatiblizing coating on at least a portion of the abrasion-resistant coating; a photochromic coating comprising a photochromic material according to various non-limiting embodiments disclosed herein on at least a portion of the primer or compatiblizing coating; a transitional coating on at least a portion of the photochromic coating; and an abrasion-resistant coating on at least a portion of the transitional coating. Further, according to this non-limiting embodiment, the photochromic article may also comprise, for example, an antireflective coating that is connected to a surface of the substrate and/or a polarizing coating or film that is connected to a surface of the substrate.

Non-limiting methods of making photochromic compositions and photochromic articles, such as optical elements, according to various non-limiting embodiments disclosed herein will now be discussed. One non-limiting embodiment provides a method of making a photochromic composition, the method comprising incorporating a photochromic material into at least a portion of an organic material. Non-limiting methods of incorporating photochromic materials into an organic material include, for example, mixing the photochromic material into a solution or melt of a polymeric, oligomeric, or monomeric material, and subsequently at least partially setting the polymeric, oligomeric, or monomeric material (with or without bonding the photochromic material to the organic material); and imbibing the photochromic material into the organic material (with or without bonding the photochromic material to the organic material).

Another non-limiting embodiment provides a method of making a photochromic article comprising connecting a photochromic material according to various non-limiting embodiments discussed above, to at least a portion of a substrate. For example, if the substrate comprises a polymeric material, the photochromic material may be connected to at least a portion of the substrate by at least one of the cast-in-place method and by imbibition. For example, in the cast-in-place method, the photochromic material may be mixed with a polymeric solution or melt, or other oligomeric and/or monomeric solution or mixture, which are subsequently cast into a mold having a desired shape and at least partially set to form the substrate. Optionally, according to this non-limiting embodiment, the photochromic material may be bonded to a portion of the polymeric material of the substrate, for example, by co-polymerization with a monomeric precursor thereof. In the imbibition method, the photochromic material may be diffused into the polymeric material of the substrate after it is formed, for example, by immersing a substrate in a solution containing the photochromic material, with or without heating. Thereafter, although not required, the photochromic material may be bonded with the polymeric material.

Other non-limiting embodiments disclosed herein provide a method of making an optical element comprising connecting a photochromic material to at least a portion of a substrate by at least one of in-mold casting, coating and lamination. For example, according to one non-limiting embodiment, wherein the substrate comprises a polymeric material, the photochromic material may be connected to at least a portion of a substrate by in-mold casting. According to this non-limiting embodiment, a coating composition comprising the photochromic material, which may be a liquid coating composition or a powder coating composition, is applied to the surface of a mold and at least partially set. Thereafter, a polymer solution or melt, or oligomeric or monomeric solution or mixture is cast over the coating and at least partially set. After setting, the coated substrate is removed from the mold. Non-limiting examples of powder coatings in which the photochromic materials according to various non-limiting embodiments disclosed herein may be employed are set forth in U.S. Pat. No. 6,068,797 at col. 7, line 50 to col. 19, line 42, which disclosure is hereby specifically incorporated by reference herein.

According to still another non-limiting embodiment, wherein the substrate comprises a polymeric material or an inorganic material such as glass, the photochromic material may be connected to at least a portion of a substrate by coating. Non-limiting examples of suitable coating methods include spin coating, spray coating (e.g., using a liquid or powder coating), curtain coating, roll coating, spin and spray coating, over-molding, and combinations thereof. For example, according to one non-limiting embodiment, the photochromic material may be connected to the substrate by over-molding. According to this non-limiting embodiment, a coating composition comprising the photochromic material (which may be a liquid coating composition or a powder coating composition as previously discussed) may be applied to a mold and then the substrate may be placed into the mold such that the substrate contacts the coating causing it to spread over at least a portion of the surface of the substrate. Thereafter, the coating composition may be at least partially set and the coated substrate may be removed from the mold. Alternatively, over-molding may be done by placing the substrate into a mold such that an open region is defined between the substrate and the mold, and thereafter injecting a coating composition comprising the photochromic material into the open region. Thereafter, the coating composition may be at least partially set and the coated substrate may be removed from the mold.

Additionally or alternatively, a coating composition (with or without a photochromic material) may be applied to a substrate (for example, by any of the foregoing methods), the coating composition may be at least partially set, and thereafter, a photochromic material may be imbibed (as previously discussed) into the coating composition.

According to yet another non-limiting embodiment, wherein the substrate comprises a polymeric material or an inorganic material such as glass, the photochromic material may be connected to at least a portion of a substrate by lamination. According to this non-limiting embodiment, a film comprising the photochromic material may be adhered or otherwise connect to a portion of the substrate, with or without an adhesive and/or the application of heat and pressure. Thereafter, if desired, a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include for example and without limitation, combining a photochromic material with a polymeric solution or oligomeric solution or mixture, casting or extruding a film therefrom, and, if required, at least partially setting the film. Additionally or alternatively, a film may be formed (with or without a photochromic material) and imbibed with the photochromic material (as discussed above).

Further, various non-limiting embodiments disclosed herein contemplate the use of various combinations of the forgoing methods to form photochromic articles according to various non-limiting embodiments disclosed herein. For example, and without limitation herein, according to one non-limiting embodiment, a photochromic material may be connected to substrate by incorporation into an organic material from which the substrate is formed (for example, using the cast-in-place method and/or imbibition), and thereafter a photochromic material (which may be the same or different from the aforementioned photochromic material) may be connected to a portion of the substrate using the in-mold casting, coating and/or lamination methods discussed above.

Further, it will be appreciated by those skilled in the art that the photochromic compositions and articles according to various non-limiting embodiments disclosed herein may further comprise other additives that aid in the processing and/or performance of the composition or article. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

According to various non-limiting embodiments, the photochromic materials described herein may be used in amounts (or ratios) such that the organic material or substrate into which the photochromic materials are incorporated or otherwise connected exhibits desired optical properties. For example, the amount and types of photochromic materials may be selected such that the organic material or substrate may be clear or colorless when the photochromic material is in the closed-form (i.e., in the bleached or unactivated state) and may exhibit a desired resultant color when the photochromic material is in the open-form (that is, when activated by actinic radiation). The precise amount of the photochromic material to be utilized in the various photochromic compositions and articles described herein is not critical provided that a sufficient amount is used to produce the desired effect. It should be appreciated that the particular amount of the photochromic material used may depend on a variety of factors, such as but not limited to, the absorption characteristics of the photochromic material, the color and intensity of the color desired upon activation, and the method used to incorporate or connect the photochromic material to the substrate. Although not limiting herein, according to various non-limiting embodiments disclosed herein, the amount of the photochromic material that is incorporated into an organic material may range from 0.01 to 40 weight percent based on the weight of the organic material.

Various non-limiting embodiments disclosed herein will now be illustrated in the following non-limiting examples.

EXAMPLES

In Part I of the Examples, the synthetic procedures used to make photochromic materials according to certain non-limiting embodiments disclosed herein are set forth in Examples 1-13. In Part II, the formation of methacrylate test chips incorporating certain photochromic materials as described herein, along with comparative photochromic materials, and testing procedures to determine fade rate ($T_{1/2}$), and saturated optical density are described.

Part I: Synthetic Procedures

Example 1

Step 1

Potassium t-butoxide (68.8 grams) was weighed into a reaction flask equipped with a mechanical stirrer, placed under a nitrogen atmosphere and 700 milliliters (mL) of toluene was added followed by 4,4'-difluorobenzophenone (100 grams). The reaction mixture was stirred mechanically and heated to 70° C. A solution of dimethyl succinate (80 grams) in 100 mL of toluene was added to the reaction mixture over a 60 minute period. The reaction mixture was heated at 70° C. for 4 hours. After cooling to room temperature, the reaction mixture was poured into 500 mL of water and the toluene layer discarded. The aqueous layer was extracted with diethyl ether (1×400 mL) to remove the neutral products, and then acidified the aqueous layer with concentrated HCl. A brownish-yellow oily solid was obtained from the aqueous layer, and was extracted with 3×300 mL of ethyl acetate. The organic layers were combined, washed with saturated NaCl solution (1×500 mL) and dried over anhydrous sodium sulfate. Removal of the solvent by rotary evaporation yielded 122 grams of 4,4-di(4-fluorophenyl)-3-methoxycarbonyl-3-butenoic acids as a brownish oily solid. This material was not purified further but was used directly in the next step.

Step 2

The product of Step 1 (4,4-di(4-fluorophenyl)-3-methoxycarbonyl-3-butenoic acids, 122 grams) and acetic anhydride (250 mL) were added to a reaction flask. The reaction mixture was heated to reflux for 5 hours under a nitrogen atmosphere. The reaction mixture was cooled to room temperature and subsequently poured into 1200 mL of water. The resulting precipitate was collected by vacuum filtration and washed with cold water yielding 110 grams of 1-(4-fluorophenyl)-2-methoxycarbonyl-4-acetoxy-6-fluoronaphthalene. The product was used without further purification in the subsequent reaction.

Step 3

1-(4-Fluorophenyl)-2-methoxycarbonyl-4-acetoxy-6-fluoronaphthalene from Step 2 (110 grams) and 400 mL of methanol were combined in a reaction flask. Added 5 mL of concentrated HCl to the reaction flask, and heated to reflux for 4 hours under a nitrogen atmosphere. The reaction mixture was cooled to room temperature and then at 0° C. White crystals of the desired product (1-(4-fluorophenyl)-2-methoxycarbonyl-4-hydroxy-6-fluoronaphthalene, 65 grams) were obtained, and subsequently filtered off and dried under vacuum. This material was not purified further but was used directly in the next step.

Step 4

The product of Step 3 (1-(4-fluorophenyl)-2-methoxycarbonyl-4-hydroxy-6-fluoronaphthalene, 39.4 grams) was added to a reaction flask containing 300 mL of tetrahydrofuran. The resulting mixture was cooled in an ice water bath and stirred under a nitrogen atmosphere. 167 mL of a methyl magnesium bromide solution (3M in diethyl ether) was added dropwise over thirty minutes. The resulting yellow reaction mixture was warmed to room temperature, and stirred overnight. The reaction mixture was poured into 400 mL of water, and neutralized with concentrated HCl till acidic. The mixture was extracted with three 300 mL portions of ether, and the organic portions were combined and washed with 1 L of saturated NaCl solution. The organic layer was dried over anhydrous sodium sulfate and concentrated by rotary evaporation. The resulting brown oil (37.8 grams) was transferred into a reaction vessel (fitted with a Dean-Stark trap) containing 300 mL of xylene to which five drops of dodecylbenzene sulfonic acid were added. The reaction mixture was heated to reflux for 3 hours and cooled. The xylene was removed via rotary evaporation to yield 35 grams of 3,9-difluoro-7,7-dimethyl-5-hydroxy-7H-benzo[C]fluorene as a light brown oil. This material was not purified further but was used directly in the next step.

Step 5

The product of Step 4 (3,9-difluoro-7,7-dimethyl-5-hydroxy-7H-benzo[C]fluorene, 7.55 grams), 1,1-di(4-methoxyphenyl)-2-propyn-1-ol (6.84 grams, the product of Example 1, step 1 of U.S. Pat. No. 5,458,814, which example is hereby specifically incorporated by reference herein), 5 drops of methane sulfonic acid and 200 mL of methylene chloride were combined in a reaction flask and stirred at room temperature under a nitrogen atmosphere. After two hours, the reaction mixture was washed carefully with a mixture of 100 mL of a saturated sodium bicarbonate solution and 100 mL of water. The organic layer was separated, dried over sodium sulfate, and concentrated by rotary evaporation to get a brown solid. This brown solid was purified by crystallization from ether to yield 7.1 grams of a yellowish-white solid. An NMR spectrum showed the product to have a structure consistent with 3,3-di(4-methoxyphenyl)-6,11-difluoro-13,13-dimethyl-3H,13H-indeno[2',3':3,4]naphtho[1,2-b]pyran.

Example 2

Step 1

Anisole (27.5 grams), 4-fluorobenzoyl chloride (35 grams) and dichloromethane (250 mL) were combined in a reaction flask. Aluminum chloride (30.8 grams) was added to the reaction mixture slowly over 20 minutes. Stirred the reaction mixture at room temperature for two hours and then poured it into a mixture of 70 mL concentrated HCl and 500 mL of water. The layers were phase separated and the aqueous layer was extracted with 2 portions of dichloromethane (300 mL each). The organic portions were combined and washed with saturated aqueous sodium bicarbonate (400 mL). The organic layer was dried over anhydrous sodium sulfate and evaporated to yielding 48.0 grams of 4-fluoro-4'-methoxy-benzophenone as a white solid. This material was not purified further but was used directly in the next step.

Step 2

4-Fluoro-4'-methoxy-benzophenone from Step 1 (126.7 grams) and acetylene saturated N,N-dimethylformamide (380 mL) were combined in a reaction flask. Sodium acetylide solution (9 weight % in toluene, 343 grams) was added to the reaction mixture dropwise over 45 minutes. The reaction mixture was stirred at room temperature for 1 hour and then poured into ice water (600 mL). The layers were phase separated and the aqueous layer was extracted with three portions of diethyl ether (200 mL). The organic layers were combined and washed with saturated aqueous $NH_4Cl$ (200 mL), saturated aqueous NaCl (200 mL), and saturated aqueous sodium bicarbonate (200 mL). The organic layer was dried over anhydrous sodium sulfate and evaporated to an amber colored oil yielding 136.6 grams of 1-(4-fluorophenyl)-1-(4-methoxyphenyl)-2-propyn-1-ol. This material was not purified further but was used directly in the next step.

Step 3

The product of Step 2 (1-(4-fluorophenyl)-1-(4-methoxyphenyl)-2-propyn-1-ol, 5.8 grams), the product of Example 1, step 4 (3,9-difluoro-7,7-dimethyl-5-hydroxy-7H-benzo[C]fluorene, 6.7 grams), 7 drops of methane sulfonic acid and 250 mL of methylene chloride were combined in a reaction flask and stirred at room temperature under a nitrogen atmosphere. After two hours, an additional 0.7 grams of the 1-(4-fluorophenyl)-1-(4-methoxyphenyl)-2-propyn-1-ol and 3 drops of methane sulfonic acid was added to the reaction mixture. The reaction mixture was stirred at room temperature for 1 hour more. Subsequently, the reaction mixture was washed carefully with a mixture of 250 mL of a saturated sodium bicarbonate solution and 250 mL of water. The organic layer was separated, dried over sodium sulfate, and concentrated by rotary evaporation to get a brownish-red oil. This brownish-red oil was purified by crystallization from ether to yield 8.4 grams of a yellowish-white solid. An NMR spectrum showed the product to have a structure consistent with 3-(4-fluorophenyl)-3-(4-methoxyphenyl)-6,11-difluoro-13,13-dimethyl-3H,13H-indeno[2',3':3,4]naphtho[1,2-b]pyran.

Example 3

The product of Example 1, Step 4 (3,9-difluoro-7,7-dimethyl-5-hydroxy-7H-benzo[C]fluorene, 5.7 grams), 1-phenyl-1-(4-morpholinophenyl)-2-propyn-1-ol (5.7 grams), 4 drops of dodecyl benzene sulfonic acid and 250 mL of chloroform were combined in a reaction flask and stirred at reflux temperatures under a nitrogen atmosphere. After one hour, an additional 0.5 grams of the 1-phenyl-1-(4-morpholinophenyl)-2-propyn-1-ol and 1 drop of dodecyl benzene sulfonic acid were added to the reaction mixture. The reaction mixture was heated at reflux for 2 hours more, and then cooled to room temperature. The reaction mixture was washed carefully with a mixture of 100 mL of a saturated sodium bicarbonate solution and 100 mL of water. The organic layer was separated, dried over sodium sulfate, and concentrated by rotary evaporation. The residue was chromatographed on a silica gel column using a mixture of hexane, methylene chloride and ethyl acetate (50/45/5) as the eluant. Photochromic fractions were collected and concentrated by rotary evaporation to obtain a bluish solid (7.5 grams). The blue solid was further purified by crystallization from ether to yield 5.7 grams of a white solid. An NMR spectrum showed the product to have a structure consistent with 3-(4-morpholinophenyl)-3-phenyl-6,11-difluoro-13,13-dimethyl-3H,13H-indeno[2',3':3,4]naphtho[1,2-b]pyran.

Example 4

The product of Example 1, Step 4 (3,9-difluoro-7,7-dimethyl-5-hydroxy-7H-benzo[C]fluorene, 5.7 grams), 1-phenyl-1-(4-piperdinophenyl)-2-propyn-1-ol (5.6 grams), 8 drops of methane sulfonic acid and 200 mL of chloroform were combined in a reaction flask and stirred at reflux temperatures under a nitrogen atmosphere. After two hour, an additional 0.6 grams of the 1-phenyl-1-(4-piperidinophenyl)-2-propyn-1-ol and 6 drops of dodecyl benzene sulfonic acid were added to the reaction mixture. The reaction mixture was heated at reflux for 2 hours more, and then cooled to room temperature. The reaction mixture was washed carefully with a mixture of 100 mL of a saturated sodium bicarbonate solution and 100 mL of water. The organic layer was separated, dried over sodium sulfate, and concentrated by rotary evaporation. The residue was chromatographed on a silica gel column using a mixture of hexane and ethyl acetate (95/5) as the eluant. Photochromic fractions were collected and concentrated by rotary evaporation to obtain a bluish-white foam (5.9 grams). The bluish-white foam was further purified by crystallization from ether to yield 2.25 grams of a white solid. An NMR spectrum showed the product to have a structure consistent with 3-phenyl-3-(4-piperidinophenyl)-6,11-difluoro-13,13-dimethyl-3H,13H-indeno[2',3':3,4]naphtho[1,2-b]pyran.

Example 5

The product of Example 1 Step 4 (3,9-difluoro-7,7-dimethyl-5-hydroxy-7H-benzo[C]fluorene, 7.0 grams), 1,1-di(4-fluorophenyl)-2-propyn-1-ol (5.7 grams), 10 drops of methane sulfonic acid, 20 drops of trifluoroacetic acid and 400 mL of methylene chloride were combined in a reaction flask and stirred at room temperature under a nitrogen atmosphere. After two hours, an additional 1.5 grams of the 1,1-di(4-fluorophenyl)-2-propyn-1-ol and 10 drops of methane sulfonic acid was added to the reaction mixture. The reaction mixture was stirred at room temperature for 6 hours more. Subsequently, the reaction mixture was washed carefully with a mixture of 250 mL of a saturated sodium bicarbonate solution and 250 mL of water. The organic layer was separated, dried over sodium sulfate, and concentrated by rotary evaporation to get a red oil. This red oil was purified by crystallization from ether to yield 6.0 grams of a yellowish-white solid. An NMR spectrum showed the product to have a structure consistent with 3,3-di(4-fluorophenyl)-6,11-difluoro-13,13-dimethyl-3H,13H-indeno[2',3':3,4]naphtho[1,2-b]pyran.

Example 6

Step 1

The procedures of Steps 1-4 of Example 1 were followed except that 4,4'-dichlorobenzophenone (112 grams) was used in place of 4,4'-difluorobenzophenone to produce 3,9-dichloro-7,7-dimethyl-5-hydroxy-7H-benzo[C]fluorene.

Step 2

The product of Step 1 (3,9-dichloro-7,7-dimethyl-5-hydroxy-7H-benzo[C]fluorene, 8.45 grams), 1,1-di(4-methoxyphenyl)-2-propyn-1-ol (6.84 grams), 5 drops of methane sulfonic acid and 200 mL of methylene chloride were combined in a reaction flask and stirred at room temperature under a nitrogen atmosphere. After two hours, the reaction mixture was washed carefully with a mixture of 100 mL of a saturated sodium bicarbonate solution and 100 mL of water. The organic layer was separated, dried over sodium sulfate, and concentrated by rotary evaporation to get a brown solid. This brown solid was purified by crystallization from ether to yield 7.4 grams of a yellowish-white solid. An NMR spectrum showed the product to have a structure consistent with 3,3-di(4-methoxyphenyl)-6,11-dichloro-13,13-dimethyl-3H,13H-indeno[2',3':3,4]naphtho[1,2-b]pyran.

Example 7

The product of Example 2 Step 2 (1-(4-fluorophenyl)-1-(4-methoxyphenyl)-2-propyn-1-ol, 3.4 grams), the product of Example 6, Step 1 (3,9-dichloro-7,7-dimethyl-5-hydroxy-7H-benzo[C]fluorene, 4.0 grams), 8 drops of methane sulfonic acid and 250 mL of methylene chloride were combined in a reaction flask and stirred at room temperature under a nitrogen atmosphere for two hours. Subsequently, the reaction mixture was washed carefully with a mixture of 250 mL of a saturated sodium bicarbonate solution and 250 mL of water. The organic layer was separated, dried over sodium sulfate, and concentrated by rotary evaporation to get a brownish-red oil. This brownish-red oil was purified by crystallization from ether and hexane mixture (1:1) to yield 4.6 grams of a yellowish-white solid. An NMR spectrum showed the product to have a structure consistent with 3-(4-fluorophenyl)-3-(4-methoxyphenyl)-6,11-dichloro-13,13-dimethyl-3H,13H-indeno[2',3':3,4]naphtho[1,2-b]pyran.

Example 8

The product of Example 6, Step 1 (3,9-dichloro-7,7-dimethyl-5-hydroxy-7H-benzo[C]fluorene, 3.0 grams), 1,1-di(4-fluorophenyl)-2-propyn-1-ol (3.8 grams), 7 drops of methane sulfonic acid, 20 drops of trifluoroacetic acid and 250 mL of methylene chloride were combined in a reaction flask and stirred at room temperature under a nitrogen atmosphere. After four hours, an additional 2.0 grams of the 1,1-di(4-fluorophenyl)-2-propyn-1-ol and 7 drops of methane sulfonic acid was added to the reaction mixture. The reaction mixture was stirred overnight at room temperature. Subsequently, the reaction mixture was washed carefully with a mixture of 200 mL of a saturated sodium bicarbonate solution and 200 mL of water. The organic layer was separated, dried over sodium sulfate, and concentrated by rotary evaporation to get a red oil. This red oil was purified by crystallization from ether to yield 1.6 grams of a yellowish-white solid. An NMR spectrum showed the product to have a structure consistent with 3,3-di(4-fluorophenyl)-6,11-dichloro-13,13-dimethyl-3H,13H-indeno[2',3':3,4]naphtho[1,2-b]pyran.

Example 9

Step 1

The product of Example 6, Step 1 (3,9-dichloro-7,7-dimethyl-5-hydroxy-7H-benzo[C]fluorene, 10.0 g) was placed in a reaction flask under a nitrogen atmosphere and 100 mL of anhydrous 1-methyl-2-pyrrolidinone and CuCN (4.5 g) were added to the reaction mixture. The reaction mixture was heated at reflux for 24 hours and then cooled to room temperature. To the resulting mixture was added 100 mL of 6M HCl and the mixture was stirred for 10 minutes. The mixture was washed with 150 ml portions of ethyl acetate three times. The organic extracts were combined and the solvent was removed by rotary evaporation to give 7.2 g of a gray solid. NMR spectra showed the product to have a structure consistent with 3,9-dicyano-7,7-dimethyl-5-hydroxy-7H-benzo[C]fluorene.

Step 2

The product of Step 1 (3,9-dicyano-7,7-dimethyl-5-hydroxy-7H-benzo[C]fluorene, 1.5 grams), 1,1-di(4-fluorophenyl)-2-propyn-1-ol (2.0 grams), 5 drops of methane sulfonic acid, 40 drops of trifluoroacetic acid and 250 mL of methylene chloride were combined in a reaction flask and stirred at room temperature under a nitrogen atmosphere. After two hours, an additional 2.0 grams of the 1,1-di(4-fluorophenyl)-2-propyn-1-ol and 4 drops of methane sulfonic acid was added to the reaction mixture. The reaction mixture was stirred for four hours at room temperature. Subsequently, the reaction mixture was washed carefully with a mixture of 250 mL of a saturated sodium bicarbonate solution and 250 mL of water. The organic layer was separated, dried over sodium sulfate, and concentrated by rotary evaporation to get a brown solid. This brown solid was purified by crystallization from ether to yield 1.7 grams of a white solid. An NMR spectrum showed the product to have a structure consistent with 3,3-di(4-fluorophenyl)-6,11-dicyano-13,13-dimethyl-3H,13H-indeno[2',3':3,4]naphtho[1,2-b]pyran.

Example 10

Step 1

3,9-Dicyano-7,7-dimethyl-5-hydroxy-7H-benzo[C]fluorene from Example 9, Step 1 (5.0 g), 1.0 mL of aqueous HCl, and 100 mL of methanol were combined in a flask and heated at reflux for 24 hours. The reaction mixture was cooled and the resulting precipitate was collected by vacuum filtration and washed with cold methanol yielding 4.9 g of a white solid. NMR spectra showed the product to have a structure consistent with 3,9-dicarboxy-7,7-dimethyl-5-hydroxy-7H-benzo[C]fluorene.

Step 2

3,9-Dicarboxy-7,7-dimethyl-5-hydroxy-7H-benzo[C]fluorene from Step 1 (4.9 g), 1.0 mL of aqueous HCl, and 100 mL of methanol were combined in a flask and heated at reflux for 24 hours. The reaction mixture was cooled and the resulting precipitate was collected by vacuum filtration and washed with cold methanol yielding 4.8 g of a white solid. NMR spectra showed the product to have a structure consistent with 3,9-dimethoxycarbonyl-7,7-dimethyl-5-hydroxy-7H-benzo[C]fluorene.

Step 3

The procedure of Example 6, Step 2 was followed except that 3,9-dimethoxycarbonyl-7,7-dimethyl-5-hydroxy-7H-benzo[C]fluorene was used in place of 3,9-dichloro-7,7-dimethyl-5-hydroxy-7H-benzo[C]fluorene to produce 3,3-di(4- methoxyphenyl)-6,11-di(methoxycarbonyl)-13,13-dimethyl-3H,13H-indeno[2',3':3,4]naphtho[1,2-b]pyran.

Example 11

The product of Example 10, Step 2 (3,9-dimethoxycarbonyl-7,7-dimethyl-5-hydroxy-7H-benzo[C]fluorene, 1.6 grams), 1,1-di(4-fluorophenyl)-2-propyn-1-ol (2.1 grams), 5 drops of methane sulfonic acid, 20 drops of trifluoroacetic acid and 250 mL of methylene chloride were combined in a reaction flask and stirred at room temperature under a nitrogen atmosphere. After two hours, an additional 1.1 grams of the 1,1-di(4-fluorophenyl)-2-propyn-1-ol and 10 drops of trifluoroacetic acid was added to the reaction mixture. The reaction mixture was stirred overnight at room temperature. Subsequently, the reaction mixture was washed carefully with a mixture of 250 mL of a saturated sodium bicarbonate solution and 250 mL of water. The organic layer was separated, dried over sodium sulfate, and concentrated by rotary evaporation to get a brown solid. This brown solid was chromatographed on a silica gel column using a mixture of hexane and ethyl acetate (85/15) as the eluant. The photochromic fractions were collected and concentrated by rotary evaporation to obtain a red foam. This red foam was further purified by crystallization from ether to yield 0.44 grams of a white solid. An NMR spectrum showed the product to have a structure consistent with 3,3-di(4-fluorophenyl)-6,11-di(methoxycarbonyl)-13,13-dimethyl-3H,13H-indeno[2',3':3,4]naphtho[1,2-b]pyran.

Example 12

Step 1

Potassium t-butoxide (50.1 grams) and 100.0 grams of 4-bromobenzophenone were added to a reaction flask containing 500 mL of toluene under a nitrogen atmosphere. To the mixture was added dimethyl succinate (110.1 grams) dropwise over 1 hour period. The mixture was stirred for 5 hours at room temperature. The resulting mixture was poured into 300 mL of water and vigorously stirred for 20 minutes. The aqueous and organic phases separated and the organic phases were extracted with 100 mL portions of water three times. The combined aqueous layers were washed with 150 ml portions of chloroform three times. The aqueous layer was acidified to pH 2 with 6N HCl and a precipitate formed. The aqueous layer was extracted with three 100 mL portions of chloroform. The organic extracts were combined and concentrated by rotary evaporation. An NMR spectrum of the resulting oil showed the product to have structures consistent with a mixture of (E and Z) 4-phenyl-4-(4-bromophenyl)-3-methoxycarbonyl-3-butenoic acids.

Step 2

The crude half-esters from Step 1 (100.0 grams), 60 mL of acetic anhydride, and 300 mL of toluene were added to a reaction flask under a nitrogen atmosphere. The reaction mixture was heated to 110° C. for 6 hours and cooled to room temperature, and the solvents (toluene and acetic anhydride) were removed by rotary evaporation. The residue was dissolved in 300 mL of methylene chloride and 200 mL of water. Solid sodium carbonate was added to the biphasic mixture until bubbling ceased. The layers separated and the aqueous layer was extracted with 50 mL portions of methylene chloride. The organic extracts were combined and the solvent was removed by rotary evaporation to yield thick red oil. The oil was dissolved in warm methanol and chilled at 0° C. for 2 hours. The resulting crystals were collected by vacuum filtration and washed with cold methanol to yield a mixture of 1-(4-bromophenyl)-2-methoxycarbonyl-4-acetoxy-naphthalene and 1-phenyl-2-methoxycarbonyl-4-acetoxy-6-bromonaphthalene. The mixture was used without further purification in subsequent reaction.

Step 3

The mixture (50 grams) from Step 2 was weighed into a reaction flask under a nitrogen atmosphere and 300 mL of anhydrous tetrahydrofuran (THF) was added. Methyl magnesium chloride (180 mL of 3.0M in THF) was added to the reaction mixture over a 1 hour period. The reaction mixture was stirred overnight and then poured into 300 mL of a 1:1 mixture of ice and 1N HCl. The mixture was extracted with chloroform (three times with 300 mL). The organic extracts were combined, washed with saturated aqueous NaCl solution (400 mL) and dried over anhydrous sodium sulfate. Removal of the solvent by rotary evaporation yielded 42.0 grams of a mixture of 1-(4-bromophenyl)-2-(1-methyl-1-hydroxyethyl)-4-hydroxy-naphthalene and 1-phenyl-2-(1-methyl-1-hydroxyethyl)-4-hydroxy-6-bromonaphthalene.

Step 4

The mixture from Step 3 (30.0 grams) was placed in a reaction flask equipped with a Dean-Stark trap and 150 mL of toluene was added. The reaction mixture was stirred under a nitrogen atmosphere and dodecylbenzene sulfonic acid (about 0.5 mL) was added. The reaction mixture was heated at reflux temperatures for 2 hours and cooled to room temperature. Removal of the solvent by rotary evaporation yielded a mixture of 7,7-dimethyl-9-bromo-7H-benzo[C]fluorene-5-ol and 3-bromo-7,7-dimethyl-7H-benzo[C]fluorene-5-ol. The product mixture was used without further purification in subsequent reaction.

Step 5

The mixture from Step 4 (10.0 grams) was placed in a reaction flask under a nitrogen atmosphere and 100 mL of anhydrous 1-methyl-2-pyrrolidinone (NMP) was added. CuCN (4.5 grams) was added to the reaction mixture. The reaction mixture was heated at reflux temperatures for 4 hours and cooled to room temperature. To the resulting mixture was added 100 mL of 6M HCl and the mixture was stirred for 10 minutes. The mixture was washed with 150 ml portions of ethyl acetate three times. The organic extracts were combined and the solvent was removed by rotary evaporation to give 8.2 grams of grey solid. An NMR spectrum showed the product to have a structure consistent with a mixture of 7,7-dimethyl-9-cyano-7H-benzo[C]fluoren-5-ol and 3-cyano-7,7-dimethyl-7H-benzo[C]fluoren-5-ol. The product mixture was used without further purification in subsequent reaction.

Step 6

The product of Step 5 (mixture of 3-cyano-7,7-dimethyl-5-hydroxy-7H-benzo[C]fluorene and 9-cyano-7,7-dimethyl-5-hydroxy-7H-benzo[C]fluorene, 5.0 grams), 1,1-di(4-fluorophenyl)-2-propyn-1-ol (7.3 grams), 15 drops of methane sulfonic acid, 40 drops of trifluoroacetic acid and 500 mL of methylene chloride were combined in a reaction flask and stirred at room temperature under a nitrogen atmosphere. After four hours, the reaction mixture was washed carefully with a mixture of 500 mL of a saturated sodium bicarbonate solution and 500 mL of water. The organic layer was separated, dried over sodium sulfate, and concentrated by rotary evaporation to get a red oil. This red oil was chromatographed on a silica gel column using a mixture of hexane, methylene chloride and ethyl acetate (80/17/3) as the eluant. The photochromic fractions ($R_f$=0.42 when the eluant is 80/17/3 hexane/methylene chloride/ethyl acetate) were collected and concentrated by rotary evaporation to obtain a red solid (0.54 grams). This red solid was further purified by crystallization from ether to yield 0.4 grams of a white solid. An NMR spectrum showed the product to have a structure consistent with 3,3-di(4-fluorophenyl)-6-cyano-13,13-dimethyl-3H, 13H-indeno[2',3':3,4]naphtho[1,2-b]pyran.

Example 13

Step 1

The mixture of Example 12, Step 5 (7,7-dimethyl-9-cyano-7H-benzo[C]fluoren-5-ol and 3-cyano-7,7-dimethyl-7H-benzo[C]fluoren-5-ol, 30.0 grams) was placed in a reaction flask under a nitrogen atmosphere and NaOH (20 grams) was added. To the mixture, ethanol (100 mL) and water (100 mL) were added. The reaction mixture was heated at reflux temperatures for 24 hours and cooled to room temperature. The resulting mixture was poured into 200 mL of a 1:1 mixture of ice and 6N HCl and stirred vigorously for 15 minutes. The mixture was washed with 150 ml portions of ethyl acetate three times. The organic extracts were combined and the solvent was removed by rotary evaporation to give 9.2 grams of white solid. An NMR spectrum showed the products to have mixture of 5-hydroxy-7,7-dimethyl-7H-9-carboxy-benzo[C]-fluorene and 3-carboxy-5-hydroxy-7,7-dimethyl-7H-benzo[C]-fluorene. The product mixture was used without further purification in subsequent reaction.

Step 2

The mixture from step 1 (20.0 grams), 1.0 mL of aqueous HCl, and 100 mL of methanol were combined in a flask and heated at reflux temperatures for 24 hours. The reaction mixture was cooled and the resulting precipitate was collected by vacuum filtration and washed with cold methanol yielding 4.9 grams of white solid. An NMR spectrum showed the products to have mixture of 5-hydroxy-7,7-dimethyl-7H-9-methoxycarbonyl-benzo[C]-fluorene and 3-methoxycarbonyl-5-hydroxy-7,7-dimethyl-7H-benzo[C]-fluorene. The product mixture was used without further purification in subsequent reaction.

Step 3

The product of Step 2 (mixture of 3-carbomethoxy-7,7-dimethyl-5-hydroxy-7H-benzo[C]fluorene and 9-carbomethoxy-7,7-dimethyl-5-hydroxy-7H-benzo[C]fluorene, 3.0 grams), 1,1-di(4-fluorophenyl)-2-propyn-1-ol (2.3 grams), 8 drops of methane sulfonic acid and 300 mL of methylene chloride were combined in a reaction flask and stirred at room temperature under a nitrogen atmosphere. After four hours, an additional 2.0 grams of the 1,1-di(4-fluorophenyl)-2-propyn-1-ol and 4 drops of methane sulfonic acid was added to the reaction mixture. The reaction mixture was stirred overnight at room temperature. Subsequently, the reaction mixture was washed carefully with a mixture of 200 mL of a saturated sodium bicarbonate solution and 200 mL of water. The organic layer was separated, dried over sodium sulfate, and concentrated by rotary evaporation to get a red oil that foamed upon drying. This red oil was chromatographed on a silica gel column using a mixture of hexane and ethyl acetate (85/15) as the eluant. The photochromic fractions ($R_f$=0.60 when the eluant is 80/20 hexane/ethyl acetate) were collected and concentrated by rotary evaporation to obtain a red solid. This red solid was further purified by crystallization from ether to yield 0.48 grams of a white solid. An NMR spectrum showed the product to have a structure consistent with 3,3-di(4-fluorophenyl)-6-methoxycarbonyl-13,13-dimethyl-3H,13H-indeno[2'3':3,4]naphtho[1,2-b]pyran.

Part II: Testing

The photochromic performance of the photochromic materials of Examples 1-13, Comparative Example CE1-CE12, and Examples 14-22 comprising additional photochromic materials according to the present disclosure were tested using the following optical bench set-up. It will be appreciated by those skilled in the art that the photochromic materials of Examples 14-22 and Comparative Examples CE1-CE12 may be made in accordance with the teachings and examples disclosed herein with appropriate modifications, which will be readily apparent to those skilled in the art upon reading the present disclosure. Further, those skilled in the art will recognize that various modifications to the disclosed methods, as well as other methods, may be used in making the photochromic materials of Examples 1-13 without deviating from the scope of the present disclosure as set forth in the specification and claims herein.

Methacrylate Chip Procedure

A quantity of the photochromic material to be tested, calculated to yield a $1.5 \times 10^{-3}$ M solution (for spectral analysis of Examples 9-11, photochromic material solution at half concentration, i.e., a $7.5 \times 10^{-4}$ M solution, were used) was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) ("AIBN"). The photochromic material was dissolved into the monomer blend by stirring and gentle heating. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, and then lower the temperature to 60° C. for at least 2 hours. After the mold was opened, the polymer sheet was cut using a diamond blade saw into 2 inch (5.1 cm) test squares.

The test squares incorporating the photochromic materials prepared as described above were tested for photochromic response on an optical bench. Prior to testing on the optical bench, the photochromic test squares were exposed to 365 nm ultraviolet light for about 15 minutes to cause the photochromic materials therein to transform from the unactivated ground (or bleached) state to an activated (or colored) state, and then placed in a 75° C. oven for about 15 minutes to allow the photochromic material to revert back to the unactivated state. The test squares were then cooled to room temperature, exposed to fluorescent room lighting for at least 2 hours, and then kept covered (that is, in a dark environment) for at least 2 hours prior to testing on an optical bench maintained at 23° C. The bench was fitted with a 300-watt xenon arc lamp, a remote controlled shutter, a Melles Griot KG2 filter that modifies the UV and IR wavelengths and acts as a heat-sink, neutral density filter(s), and a sample holder, situated within a 23° C. water bath, in which the square to be tested was inserted. A collimated beam of light from a tungsten lamp was passed through the square at a small angle (approximately 30°) normal to the square. After passing through the square, the light from the tungsten lamp was directed to a collection sphere, where the light was blended, and on to an Ocean Optics S2000 spectrometer where the spectrum of the measuring beam was collected and analyzed. The $\lambda_{max\text{-}vis}$ is the wavelength in the visible spectrum at which the maximum absorption of the activated (colored) form of the photochromic material in the test square occurs. The $\lambda_{max\text{-}vis}$ wavelength was determined by testing the photochromic test squares in a Varian Cary 4000 UV-Visible spectrophotometer. The output signals from the detector were processed by a radiometer.

The saturated optical density ("Sat'd OD") for each test square was determined by opening the shutter from the xenon lamp and measuring the transmittance after exposing the test chip to UV radiation for 30 minutes. The $\lambda_{max\text{-}vis}$ at the Sat'd OD was calculated from the activated data measured by the S2000 spectrometer on the optical bench. The Fade Rate, as measured by the fade half life (i.e., $T_{1/2}$), is the time interval in seconds for the absorbance of the activated form of the photochromic material in the test squares to reach one half of the Sat'd OD absorbance value at room temperature (23° C.), after removal of the source of activating light. Performance Rating ("PR") is calculated from the Sat'd OD and $T_{1/2}$ by the equation:

$$PR = ((Sat'd\ OD)/T_{1/2}) \times 10{,}000.$$

Photochromic data of the photochromic materials of the present disclosure are listed below in Table 1. Photochromic data for comparative photochromic materials (i.e. photochromic indeno-fused naphthopyrans without a first electron-drawing group at the 6-position and a second electron-withdrawing group in the 11-position) are presented below in Table 2.

TABLE 1

Photochromic Materials and Test Results

| Ex. | Photochromic Material | $\lambda_{max\text{-}vis}$ (nm) | Sat'd OD | $T_{1/2}$ (sec) | PR |
|---|---|---|---|---|---|
| 1 | 3,3-di(4-methoxyphenyl)-6,11-difluoro-13,13-dimethyl-3H,13H-indeno[2',3':3,4]naphtho[1,2-b]pyran | 570 | 0.49 | 70 | 69 |
| 2 | 3-(4-fluorophenyl)-3-(4-methoxyphenyl)-6,11-difluoro-13,13-dimethyl-3H,13H-indeno[2',3':3,4]naphtho[1,2-b]pyran | 559 | 0.75 | 110 | 68 |
| 3 | 3-(4-morpholinophenyl)-3-phenyl-6,11-difluoro-13,13-dimethyl-3H,13H-indeno[2',3':3,4]naphtho[1,2-b]pyran | 599 | 0.84 | 122 | 69 |
| 4 | 3-phenyl-3-(4-piperidinophenyl)-6,11-difluoro-13,13-dimethyl-3H,13H-indeno[2',3':3,4]naphtho[1,2-b]pyran | 616 | 0.73 | 94 | 78 |
| 5 | 3,3-di(4-fluorophenyl)-6,11-difluoro-13,13-dimethyl-3H,13H-indeno[2',3':3,4]naphtho[1,2-b]pyran | 545 | 0.89 | 199 | 45 |
| 6 | 3,3-di(4-methoxyphenyl)-6,11-dichloro-13,13-dimethyl-3H,13H-indeno[2',3':3,4]naphtho[1,2-b]pyran | 572 | 0.32 | 48 | 66 |
| 7 | 3-(4-fluorophenyl)-3-(4-methoxyphenyl)-6,11-dichloro-13,13-dimethyl-3H,13H-indeno[2',3':3,4]naphtho[1,2-b]pyran | 563 | 0.52 | 68 | 77 |
| 8 | 3,3-di(4-fluorophenyl)-6,11-dichloro-13,13-dimethyl-3H,13H-indeno[2',3':3,4]naphtho[1,2-b]pyran | 547 | 0.66 | 121 | 54 |
| 9 | 3,3-di(4-fluorophenyl)-6,11-dicyano-13,13-dimethyl-3H,13H-indeno[2',3':3,4]naphtho[1,2-b]pyran | 545 | 0.23 | 30 | 76 |
| 10 | 3,3-di(4-methoxyphenyl)-6,11-di(methoxycarbonyl)-13,13-dimethyl-3H,13H-indeno[2',3':3,4]naphtho[1,2-b]pyran | 572 | 0.19 | 30 | 64 |
| 11 | 3,3-di(4-fluorophenyl)-6,11-di(methoxycarbonyl)-13,13-dimethyl-3H,13H-indeno[2',3':3,4]naphtho[1,2-b]pyran | 541 | 0.47 | 71 | 66 |
| 12 | 3,3-di(4-fluorophenyl)-6-cyano-13,13-dimethyl-3H,13H-indeno[2',3':3,4]naphtho[1,2-b]pyran | 551 | 0.49 | 52 | 94 |
| 13 | 3,3-di(4-fluorophenyl)-6-methoxycarbonyl-13,13-dimethyl-3H,13H-indeno[2',3':3,4]naphtho[1,2-b]pyran | 543 | 0.81 | 130 | 62 |
| 14 | 3-(4-fluorophenyl)-3-(4-piperidinophenyl)-6,11-difluoro-13,13-dimethyl-3H,13H-indeno[2',3':3,4]naphtho[1,2-b]pyran | 613 | 0.48 | 64 | 75 |
| 15 | 3-(4-methoxyphenyl)-3-(4-morpholinophenyl)-6,11-difluoro-13,13-dimethyl-3H,13H-indeno[2',3':3,4]naphtho[1,2-b]pyran | 604 | 0.38 | 52 | 73 |
| 16 | 3-(4-fluorophenyl)-3-(4-morpholinophenyl)-6,11-difluoro-13,13-dimethyl-3H,13H-indeno[2',3':3,4]naphtho[1,2-b]pyran | 595 | 0.58 | 74 | 78 |
| 17 | 3-(4-methylphenyl)-3-(4-morpholinophenyl)-6,11-difluoro-13,13-dimethyl-3H,13H-indeno[2',3':3,4]naphtho[1,2-b]pyran | 601 | 0.59 | 88 | 68 |
| 18 | 3-phenyl-3-(4-piperidinophenyl)-6,11-dichloro-13,13-dimethyl-3H,13H-indeno[2',3':3,4]naphtho[1,2-b]pyran | 632 | 0.47 | 58 | 82 |
| 19 | 3-(4-methoxyphenyl)-3-(5-methylthiophen-2-yl)-6,11-dichloro-13,13-dimethyl-3H,13H-indeno[2',3':3,4]naphtho[1,2-b]pyran | 591 | 0.31 | 51 | 60 |
| 20 | 3,3-diphenyl-6,11-dicyano-13,13-dimethyl-3H,13H-indeno[2',3':3,4]naphtho[1,2-b]pyran | 545 | 0.41 | 49 | 83 |
| 21 | 3-(4-morpholinophenyl)-3-phenyl-6-bromo-13,13-dimethyl-3H,13H-indeno[2',3':3,4]naphtho[1,2-b]pyran | 599 | 0.74 | 115 | 64 |
| 22 | 3-(4-methoxyphenyl)-3-phenyl-6-bromo-13,13-dimethyl-3H,13H-indeno[2',3':3,4]naphtho[1,2-b]pyran | 564 | 0.77 | 133 | 58 |

TABLE 2

Comparative Photochromic Materials and Test Results

| Ex. | Photochromic Material | $\lambda_{max\text{-}vis}$ (nm) | Sat'd OD | $T_{1/2}$ (sec) | PR |
|---|---|---|---|---|---|
| CE1 | 3,3-diphenyl-13,13-dimethyl-3H,13H-indeno[2',3':3,4]naphtho[1,2-b]pyran | 532 | 1.50 | 723 | 21 |
| CE2 | 3,3-di(4-fluorophenyl)-13,13-dimethyl-3H,13H-indeno[2',3':3,4]naphtho[1,2-b]pyran | 533 | 1.09 | 395 | 28 |
| CE3 | 3-(4-methoxyphenyl)-3-phenyl-13,13-dimethyl-3H,13H-indeno[2',3':3,4]naphtho[1,2-b]pyran | 548 | 1.34 | 343 | 39 |
| CE4 | 3-(4-fluorophenyl)-3-(4-methoxyphenyl)-13,13-dimethyl-3H,13H-indeno[2',3':3,4]naphtho[1,2-b]pyran | 547 | 1.12 | 222 | 50 |
| CE5 | 3-(4-morpholinophenyl)-3-phenyl-13,13-dimethyl-3H,13H-indeno[2',3':3,4]naphtho[1,2-b]pyran | 583 | 1.45 | 241 | 60 |
| CE6 | 3-(4-methoxyphenyl)-3-(5-methylthiophen-2-yl)-13,13-dimethyl-3H,13H-indeno[2',3':3,4]naphtho[1,2-b]pyran | 573 | 0.83 | 141 | 59 |
| CE7 | 3-(4-methoxyphenyl)-3-(4-morpholinophenyl)-13,13-dimethyl-3H,13H-indeno[2',3':3,4]naphtho[1,2-b]pyran | 586 | 0.61 | 99 | 62 |
| CE8 | 3,3-di(4-methoxyphenyl)-13,13-dimethyl-3H,13H-indeno[2',3':3,4]naphtho[1,2-b]pyran | 561 | 0.78 | 129 | 60 |
| CE9 | 3-(4-fluorophenyl)-3-(4-morpholinophenyl)-13,13-dimethyl-3H,13H-indeno[2',3':3,4]naphtho[1,2-b]pyran | 579 | 1.06 | 151 | 70 |
| CE10 | 3-(4-methylphenyl)-3-(4-morpholinophenyl)-13,13-dimethyl-3H,13H-indeno[2',3':3,4]naphtho[1,2-b]pyran | 583 | 1.06 | 168 | 63 |
| CE11 | 3-(4-fluorophenyl)-3-(4-piperidinophenyl)-13,13-dimethyl-3H,13H-indeno[2',3':3,4]naphtho[1,2-b]pyran | 595 | 0.97 | 118 | 82 |
| CE12 | 3-phenyl-3-(4-piperidinophenyl)-13,13-dimethyl-3H,13H-indeno[2',3':3,4]naphtho[1,2-b]pyran | 599 | 1.04 | 180 | 50 |

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

We claim:

1. A photochromic material representable by the following structure III:

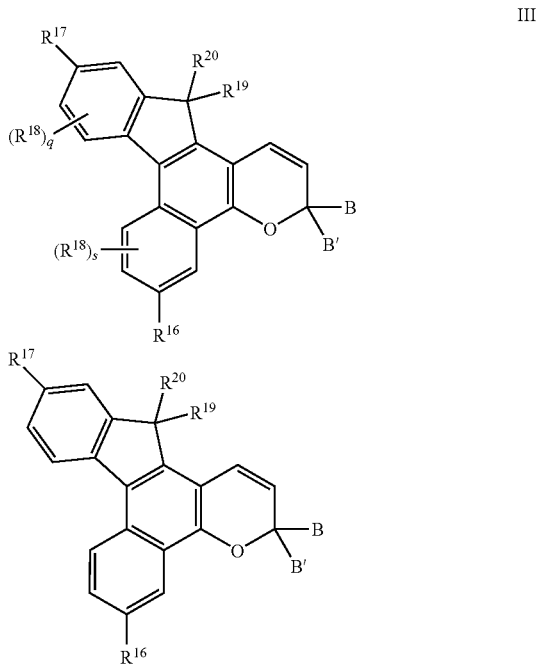

wherein
$R^{16}$ is a first electron withdrawing group having a Hammett $\sigma_p$ value of from 0.05 to 0.75;
$R^{17}$ is: hydrogen, or a second electron withdrawing group having a Hammett $\sigma_p$ value of from 0.05 to 0.75;
q is the integer 0, and s is the integer 0;
$R^{19}$ and $R^{20}$ are each independently: hydrogen; $C_1$-$C_6$ alkyl; $C_3$-$C_7$ cycloalkyl; allyl; substituted or unsubstituted phenyl; substituted or unsubstituted benzyl; chloro; fluoro; the group —C(=O)W, wherein W is hydrogen, hydroxy, $C_1$-$C_6$ alkyl, $C_1$-$C_6$ alkoxy, the unsubstituted, mono- or disubstituted aryl groups phenyl or naphthyl, phenoxy, mono- or di-($C_1$-$C_6$)alkoxy substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino; or $R^{19}$ and $R^{20}$ together form a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings, provided that substitution at the carbon to which $R^{19}$ and $R^{20}$ are attached does not comprise hydroxyl; and
B and B' are each independently an unsubstituted, or substituted aryl group that has at least one pi-bond capable of being in conjugation with the pi-system of the open form of the core indeno-fused naphthopyran structure, provided that substitution at the 13-position of the indeno-fused naphthopyran does not comprise hydroxyl.

2. The photochromic material of claim 1, wherein the first electron withdrawing group $R^{16}$ is fluoro, chloro, bromo, perfluoroalkyl, perfluoroalkoxy, cyano, —OC(=O)$R^0$, or —C(=O)—X, wherein X is hydrogen, $C_1$-$C_6$ alkyl, —$OR^1$ or —$NR^2R^3$, wherein $R^0$, $R^1$, $R^2$ and $R^3$ are each independently hydrogen, $C_1$-$C_6$ alkyl, $C_5$-$C_7$ cycloalkyl, phenyl, mono-substituted phenyl, disubstituted phenyl, alkylene glycol, or polyalkylene glycol, wherein said mono- and disubstituted phenyl substituents are $C_1$-$C_6$ alkyl or $C_1$-$C_6$ alkoxy.

3. The photochromic material of claim 1, wherein the second electron withdrawing group $R^{17}$ is fluoro, chloro, bromo, perfluoroalkyl, perfluoroalkoxy, cyano, —OC(=O)$R^4$, or —C(=O)—X, wherein X is hydrogen, $C_1$-$C_6$ alkyl, —$OR^5$ or —$NR^6R^7$, wherein $R^4$, $R^5$, $R^6$ and $R^7$ are each independently hydrogen, $C_1$-$C_6$ alkyl, $C_1$-$C_7$ cycloalkyl, phenyl, mono-substituted phenyl, disubstituted phenyl, alkylene glycol or polyalkylene glycol, wherein said mono- or di-substituted phenyl substituents are $C_1$-$C_6$ alkyl or $C_1$-$C_6$ alkoxy.

4. The photochromic material of claim 1, wherein the first electron withdrawing group $R^{16}$ and the second electron withdrawing group $R^{17}$ are each independently fluoro, chloro, bromo, cyano, or —C(=O)—$OR^8$, wherein $^8$ is $C_1$-$C_6$ alkyl, alkylene glycol or polyalkylene glycol.

5. The photochromic material of claim 4, wherein the first electron-withdrawing group $R^{16}$ is a fluoro group and the second electron-withdrawing group $R^{17}$ is a fluoro group.

6. The photochromic material of claim 4 wherein $R^{19}$ and $R^{20}$ are geminal $C_1$-$C_6$ dialkyl, wherein the B group is 4-fluorophenyl and the B' group comprises a 4-substituted phenyl, wherein the substituent on the 4-position is —$NR^{10}R^{11}$, wherein $R^{10}$ and $R^{11}$ are each independently hydrogen, $C_1$-$C_6$ alkyl, $C_5$-$C_7$ cycloalkyl, phenyl, mono-substituted phenyl or di-substituted phenyl, wherein said mono- or di-substituted phenyl substituents are $C_1$-$C_6$ alkyl or $C_1$-$C_6$ alkoxy; or R10 and $R^{11}$ come together with the nitrogen atom to form a nitrogen containing ring represented by the following graphic formula:

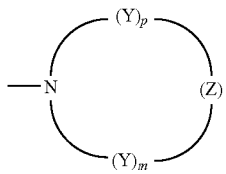

wherein each —Y— is independently chosen for each occurrence from —$CH_2$—, —CH($R^{15}$)—, —C($R^{15}$)$_2$—, —CH(aryl)-, —C(aryl)$_2$-, and —C($R^{15}$)(aryl)-, and Z is —Y—, —O—, —S—, —S(O)—, —$SO_2$—, —NH—, —N($R^{15}$)—, or —N(aryl)-, wherein each $R^{15}$ is independently $C_1$-Calkyl or hydroxy($C_1$-$C_6$)alkyl, each aryl is independently phenyl or naphthyl, m is the integer 1,2 or 3, and p is the integer 0, 1,2,or 3,provided that when p is 0, Z is —Y—.

7. The photochromic material of claim 1, wherein the groups B and B' are each independently phenyl, mono-substituted phenyl or di-substituted phenyl, wherein the phenyl substituents are independently an electron-donating group or a third electron withdrawing group.

8. The photochromic material of claim 7, wherein the groups B and B' are each independently phenyl or 4-substituted phenyl, wherein the substituent on the 4-position of the phenyl is an electron-donating group or a third electron-withdrawing group.

9. The photochromic material of claim 7, wherein at least one of the groups B and B' is a 4-substituted phenyl, wherein the substituent on the 4-position of the phenyl is fluoro or an electron-donating group chosen from $C_1$-$C_6$ alkyl, —$OR^9$ and —$NR^{10}R^{11}$, wherein $R^9$, $R^{10}$ and $R^{11}$ are each independently hydrogen, $C_1$-$C_6$ alkyl, $C_5$-$C_7$ cycloalkyl, phenyl, mono-substituted phenyl or di-substituted phenyl, wherein said mono- or di-substituted phenyl substituents are $C_1$-$C_6$ alkyl or $C_1$-$C_6$ alkoxy.

10. The photochromic material of claim 8, wherein the substituent on the 4-position of the phenyl is a third electron withdrawing group selected from chloro, bromo, perfluoroalkyl, perfluoroalkoxy, cyano, —OC(=))(=O)Z', or —C(=O)—X', where Z' and X' are each independently hydrogen, $C_1$-$C_6$ alkyl, —$OR^{12}$ or —$NR^{13}$, $R^{14}$ wherein $R^{12}$, $R^{13}$, and $R^{14}$ are each independently hydrogen, $C_1$-$C_6$ alkyl, $C_5$-$C_7$ cycloalkyl, phenyl, mono-substituted phenyl, di-substituted phenyl, alkylene glycol or polyalkylene glycol, wherein said mono- and di-substituted phenyl substituents are $C_1$-$C_6$ alkyl or alkoxy.

11. The photochromic material of claim 8, wherein the B group is 4-fluorophenyl and the B' group comprises a 4-substituted phenyl, wherein the substituent on the 4-position is —$NR^{10}R^{11}$, wherein $R^{10}$ and $R^{11}$ are each independently hydrogen, $C_1$-$C_6$ alkyl, $C_5$-$C_7$, cycloalkyl, phenyl, mono-substituted phenyl or di-substituted phenyl, wherein said mono- or di-substituted phenyl substituents are $C_1$-$C_6$ alkyl or $C_1$-$C_6$ alkoxy; or $R^{10}$ and $R^{11}$ come together with the nitrogen atom to form a nitrogen containing ring represented by the following graphic formula:

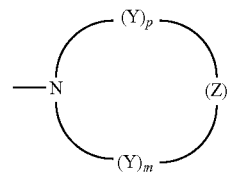

wherein each —Y— is independently chosen for each occurrence from —$CH_2$—, —C($R^{15}$)—, —C($R^{15}$)$_2$—, —CH(aryl)-, —C(aryl)$_2$-, and —C($R^{15}$)(aryl)-, and Z is —Y—, —O—, —S—, —S(O)—, —$SO_2$—, —NH—, —N($R^{15}$)—, or —N(aryl)-, wherein each $R^{15}$ is independently $C_1$-$C_6$ alkyl or hydroxy($C_1$-$C_6$)alkyl, each aryl is independently phenyl or naphthyl, m is the integer 1, 2 or 3, and p is the integer 0, 1, 2, or 3, provided that when p is 0, Z is —Y—.

12. The photochromic material of claim 11, wherein B' comprises 4-morpholinophenyl, 4-piperidinophenyl, 4(substituted piperidino)phenyl, 4-pyrrolidinophenyl, 4-(substituted pyrrolidino)phenyl, 4-piperazinophenyl, or 4-(substituted piperazino)phenyl, wherein the substitution may comprise hydroxy($C_1$-$C_6$)alkyl.

13. The photochromic material of claim 1, further comprising a geminal $C_1$-$C_6$ dialkyl substitution at the 13-position of the indeno-fused naphthopyran.

14. A photochromic article comprising:
   a substrate; and
   the photochromic material according to claim 1 connected to at least a portion of the substrate.

15. The photochromic article of claim 14, wherein the substrate comprises a polymeric material and the photochromic material is incorporated into at least a portion of the polymeric material by at least one method of blending the photochromic material with at least a portion of the polymeric material, bonding the photochromic material to at least a portion of the polymeric material, and imbibing the photochromic material into at least a portion of the polymeric material.

16. The photochromic article of claim 14, wherein the photochromic article comprises an at least partial coating connected to at least a portion of the substrates the at least partial coating comprising the photochromic material.

17. A photochromic material representable by the following structure III:

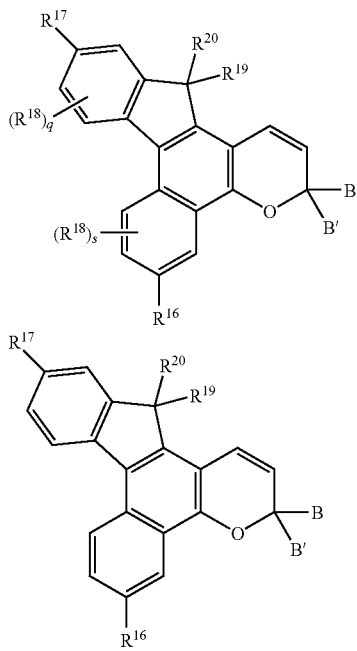

III wherein $R^{16}$ is a first electron withdrawing group chosen from fluoro, chloro, bromo, perfluoroalkyl, perfluoroalkoxy, cyano, —OC(=O)$R^{21}$, or —C(=O)—X, wherein X is hydrogen, $C_1$-$C_6$ alkyl, —OR$^{22}$, or —NR$^{23}$R$^{24}$, wherein $R^{21}$, $R^{22}$, $R^{23}$ and $R^{24}$ are each independently hydrogen, $C_1$-$C_6$ alkyl, $C_5$-$C_7$ cycloalkyl, phenyl, mono-substituted phenyl, di-substituted phenyl, alkylene glycol or polyalkylene glycol, wherein said phenyl substituents are $C_1$-$C_6$ alkyl or $C_1$-$C_6$ alkoxy;

$R^{17}$ is hydrogen, or a second electron withdrawing group chosen from fluoro, chloro, bromo, perfluoroalkyl, perfluoroalkoxy, cyano, —OC(=O)R$^{25}$ or —C(=O)—X, wherein X is hydrogen, $C_1$-$C_6$ alkyl, —OR$^{26}$ or —NR$^{27}$R$^{28}$, wherein R$^{25}$, R$^{26}$, R$^{27}$ and R$^{28}$ are each independently hydrogen, $C_1$-$C_6$ alkyl, $C_5$-C7 cycloalkyl, phenyl, mono-substituted phenyl, di-substituted phenyl, alkylene glycol or polyalkylene glycol, wherein said phenyl substituents are $C_1$-$C_6$ alkyl or $C_1$-$C_6$ alkoxy;

q is the integer 0, and s is the integer 0;

$R^{19}$ and $R^{20}$ are each independently: hydrogen; $C_1$-$C_6$ alkyl; $C_3$-$C_7$ cycloalkyl; allyl; substituted or unsubstituted phenyl; substituted or unsubstituted benzyl; chloro; fluoro; the group —C(=O)W, wherein W is hydrogen, hydroxy, $C_1$-$C_6$ alkyl, $C_1$-$C_6$ alkoxy, the unsubstituted, mono- or di-substituted aryl groups phenyl or naphthyl, phenoxy, mono- or di-($C_1$-$C_6$) alkoxy substituted phenoxy, amino, mono($C_1$-$C_6$) alkylamino, di($C_1$-$C_6$)alkylamino, phenyl amino, mono- or di ($C_1$-$C_6$)alkyl substituted phenylamino or mono- or di-($C_1$C$_6$)alkoxy substituted phenylamino; or $R^{19}$ and $R^{20}$ together form a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings, provided that substitution at the carbon to which $R^{19}$ and $R^{20}$ are attached does not comprise hydroxyl; and B and B' are each independently: an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3 -yl, dibenzofuranyl, dibenzothienyl, carbazoyl, benzopyridyl, indolinyl and fluorenyl, wherein each of the phenyl, aryl and heteroaromatic substituents are each independently: hydroxyl, a group —C(=O)R$^{40}$, wherein R$^{40}$ is —OR$^{41}$, —N(R$^{42}$)R$^{43}$, piperidino, or morpholino, wherein R" is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$) alkyl, mono($C_1$-$C_6$)alkyl substituted phenyl($C_1$-$C_3$) alkyl, mono($C_1$-$C_6$)alkoxy substituted phenyl($C_1$-$C_3$) alkyl, $C_1$-$C_6$ alkoxy($C_2$-$C_4$alkyl or $C_1$-$C_6$ haloalkyl, said halo substituent being chloro or fluoro, R$^{42}$ and R$^{43}$ are each independently $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy; an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —CH$_2$—, —(CH$_2$)$_t$—, or —[O—(CH$_2$)$_t$]$_k$—, wherein t is the integer 2, 3, 4, 5 or 6 and k is an integer from 1 to 50, the substituent being connected to an aryl group on another photochromic material;

a group represented by one of:

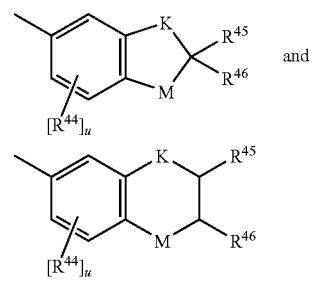

wherein K is —CH$_2$—or —O—, and M is —O— or substituted nitrogen, provided that when M is substituted nitrogen, K is —CH$_2$—, the substituted nitrogen substituents being hydrogen, $C_1$-$C_{12}$ alkyl, or $C_1$-$C_{12}$ acyl, each R$^{44}$ being independently chosen for each occurrence from $C_1$-$C_{12}$ alkyl, $C_1$-$C_{12}$ alkoxy, hydroxy, and halogen, R$^{45}$ and R$^{46}$ each being independently hydrogen or $C_1$-$C_{12}$ alkyl, and u is an integer ranging from 0 to 2; or B and B' taken together form one of a fluoren-9-ylidene, mono-, or di-substituted fluoren-9-ylidene, each of said fluoren-9-ylidene substituents being independently chosen from $C_1$-$C_{12}$ alkyl, $C_1$-$C_{12}$ alkoxy, and halogen, provided that substitution at the 13-position of the indeno-fused naphthopyran does not comprise hydroxyl.

18. The photochromic material of claim 17 that is chosen from:
(a) 3,3-di(4-methoxyphenyl)-6,11-difluoro-13,13-dimethyl-3H,13H-indeno[2',3':3,4]naphtho[1,2-b]pyran;
(b) 3-(4-fluorophenyl)-3-(4-methoxyphenyl)-6,11-difluoro-13,13-dimethyl-3H, 13H-indeno[2',3':3,4]naphtho[1,2-b]pyran;
(c) 3-(4-fluorophenyl)-3-(4-piperidinophenyl)-6,11-difluoro-13,13-dimethyl-3H,13H-indeno[2',3':3,4]naphtho[1,2-b]pyran;
(d) 3-(4-methoxyphenyl)-3-(4-morpholinophenyl)-6,11-difluoro-13,13-dimethyl-3H-13H-indeno[2',3':3,4]naphtho[1,2-b]pyran;
(e) 3-(4-fluorophenyl)-3-(4-morpholinophenyl)-6,11-difluoro-13,13-dimethyl-3H-13H-indeno[2',3':3,4]naphtho[1,2-b]pyran;
(f) 3-(4-methylphenyl)-3-(4-morpholinophenyl)-6,11-difluoro-13,13-dimethyl-3H-13H-indeno[2',3':3,4]naphtho[1,2-b]pyran;
(g) 3-phenyl-3-(4-piperidinophenyl)-6,11-difluoro-13,13-dimethyl-3H,13H-indeno[2',3':3,4]naphthol[1,2-b]pyran;
(h) 3-(4-morpholinophenyl)-3-phenyl-6,11-difluoro-13,13-dimethyl-3H,13H-indeno[2',3':3,4]naphtho[1,2-b]pyran;
(i) 3-(4-fluorophenyl)-3-(4-methoxyphenyl-6,11-dichloro-13,13-dimethyl-3H,13H-indeno[2',3':3,4]naphtho[1,2-b]pyran;
(j) 3,3-di(4-fluorophenyl)-6,11-dichloro-13,13-dimethyl-3H,13H-indeno[2',3':3,4]naphtho[1,2-b]pyran;
(k) 3-phenyl-3-(4-piperidinophenyl)-6,11-dichloro-13,13-dimethyl-3H,13H-indeno[2',3:3,4]naphtho[1,2b]pyran;
(l) 3-(4-methoxyphenyl)-3-(5-methylthiophen-2-yl)-6,11-dichloro-13,13-dimethyl-3H-13H-indeno[2',3':3,4]naphtho[1,2-b]pyran;
(m) 3,3-di(4-methoxyphenyl)-6,11-dichioro-13,13dimethyl-3H,13H-indeno[2',3':3,4]naphtho[1,2-b]pyran;
(n) 3,3-di(4-fluorophenyl)-6-cyano-13,13-dimethyl-3H, 13H-indeno[2',3':3,4]naphtho[1,2b]pyran;
(o) 3,3-di(4-fluorophenyl)-6,11-dicyano-13,13-dimethyl-3H,13H-indeno[2',3':3,4]naphtho[1,2-b]pyran;
(p) 3,3-diphenyl-6,11-dicyano-13,13-dimethyl-3H,13H-indeno[2',3':3,4]naphtho1,2-b]pyran;
(q) 3,3-di(4-fluorophenyl)-6-methoxycarbonyl-13,13-dimethyl-3H,13H-indeno[2',3':3,4]naphtho[1,2-b]pyran;
(r) 3,3-di(4-fluorophenyl)-6,11-di(methoxycarbonyl)-13,13-dimethyl-3H,13H-indeno[2',3':3,4]naphtho[1,2b]pyran;
(s) 3,3-di(4-methoxyphenyl)-6,11-di(methoxycarbonyl)-13,13-dimethyl-3H,13H-indeno[2',3':3,4]naphtho[1,2-b]pyran;
(t) 3-(4-morpholinophenyl)-3-phenyl-6-bromo-13,13-dimethyl-3H,13H-indeno[2',3':3,4] naphtho[1,2b]pyran;
(u) 3-(4-methoxyphenyl)-3-phenyl-6-bromo-13,13-dimethyl-3H,13H-indeno[2',3':3,4] naphtho[1,2-b]pyran; and
(v) 3,3-di(4-fluorophenyl)-6,11-difluoro-13,13-dimethyl-3H,13H-indeno[2',3':3,4]naphtho[1,2-b]pyran.

19. The photochromic material of claim 17, wherein the first electron withdrawing group and the second electron withdrawing group are each independently fluoro, chloro, bromo, cyano, or —C(=O)—OR$^8$, wherein R$^8$ is $C_1$-$C_6$ alkyl, alkylene glycol or polyalkylene glycol.

20. The photochromic material of claim 19, wherein R$^{16}$ is fluoro; R$^{17}$ is hydrogen or fluoro; and R$^{19}$ and R$^{20}$ are each independently $C_1$-$C_6$ alkyl.

21. The photochromic material of claim 19, wherein the groups B and B' are each independently phenyl, mono-substituted phenyl or di-substituted phenyl, wherein the substituents on the phenyl are independently an electron-donating group or a third electron withdrawing group.

22. The photochromic material of claim 21, wherein the B group is a 4-fluorophenyl and the B' group comprises a 4-Substituted phenyl, wherein the substituent in the 4-position is —NR$^{10}$R$^{11}$, wherein R$^{10}$ and R$^{11}$ are each independently hydrogen, $C_1$-$C_6$ alkyl, $C_5$-$C_7$ cycloalkyl, phenyl, mono-Substituted phenyl or di-substituted phenyl, wherein said mono- and di-substituted phenyl substituents are $C_1$-$C_6$alkyl or $C_1$-$C_6$ alkoxy, or R$^{10}$ and R$^{11}$ come together with the nitrogen atom to form a nitrogen containing ring represented by the following graphic formula:

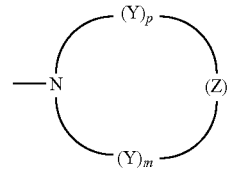

wherein each —Y— is independently chosen for each occurrence from —CH$_2$—, —CH(R$^{15}$)—, —C(R$^{15}$)$_2$—, —CH(aryl)-, —C(aryl)$_2$—, and —C(R$^{15}$)(aryl)-, and Z is —Y—, —O—, —S—, —S(O)—, —SO$_2$—, —NH—, —N(R$^{15}$)—, or —N(aryl)-, wherein each R$^{15}$ is independently $C_1$-$C_6$ alkyl or hydroxy($C_1$-$C_6$)alkyl, each aryl is independently phenyl or naphthyl, m is the integer 1, 2 or 3, and p is the integer 0, 1, 2, or 3, provided that when p is 0, Z is —Y—.

23. The photochromic material of claim 22, wherein B' comprises 4-morpholinophenyl, 4-piperidinophenyl, 4-(substituted piperidino)phenyl, 4-pyrrolidinophenyl, 4-(substituted pyrrolidino)phenyl, 4-piperazinophenyl or 4-(substituted piperazino)phenyl, wherein the substitution may comprise hydroxy($C_1$-$C_6$)alkyl.

24. The photochromic material of claim 22 wherein R$^{19}$ and R$^{20}$ are geminal $C_1$-$C_6$ dialkyl substituents.

25. The photochromic material of claim 24, wherein R$^{19}$ and R$^2$ are methyl.

* * * * *